(12) United States Patent
Silverman et al.

(10) Patent No.: US 9,090,589 B2
(45) Date of Patent: *Jul. 28, 2015

(54) SPECIFIC NNOS INHIBITORS FOR THE THERAPY AND PREVENTION OF HUMAN MELANOMA

(71) Applicants: Northwestern University, Evanston, IL (US); The Regents of the University of California, Oakland, CA (US)

(72) Inventors: Richard B. Silverman, Winnetka, IL (US); Frank L. Meyskens, Irvine, CA (US); Sun Yang, Foothill Ranch, CA (US); Haitao Ji, Salt Lake City, UT (US); Fengtian Xue, Baton Rouge, LA (US); Thomas L. Poulos, Irvine, CA (US)

(73) Assignees: Northwestern University, Evanston, IL (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/170,778

(22) Filed: Feb. 3, 2014

(65) Prior Publication Data

US 2014/0147920 A1 May 29, 2014

Related U.S. Application Data

(62) Division of application No. 13/348,819, filed on Jan. 12, 2012, now Pat. No. 8,642,282.

(60) Provisional application No. 61/461,029, filed on Jan. 12, 2011.

(51) Int. Cl.
*C12N 9/99* (2006.01)
*C07D 401/06* (2006.01)
*A61K 31/4439* (2006.01)

(52) U.S. Cl.
CPC .......... *C07D 401/06* (2013.01); *A61K 31/4439* (2013.01)

(58) Field of Classification Search
USPC .................................................. 435/18, 184
See application file for complete search history.

(56) References Cited

U.S. PATENT DOCUMENTS

| | | | |
|---|---|---|---|
| 7,470,790 B2 | 12/2008 | Silverman et al. | |
| 7,994,326 B2 | 8/2011 | Silverman et al. | |
| 8,299,100 B2 | 10/2012 | Silverman et al. | |
| 8,618,143 B1 * | 12/2013 | Silverman et al. | 514/357 |
| 8,642,282 B2 * | 2/2014 | Meyskens et al. | 435/18 |
| 2004/0259864 A1 | 12/2004 | Geneste et al. | |
| 2008/0108814 A1 | 5/2008 | Silverman et al. | |
| 2008/0176907 A1 | 7/2008 | Silverman et al. | |
| 2012/0004415 A1 | 1/2012 | Silverman et al. | |
| 2012/0088798 A1 | 4/2012 | Silverman et al. | |

\* cited by examiner

*Primary Examiner* — Ralph Gitomer
(74) *Attorney, Agent, or Firm* — Reinhart Boerner Van Deuren S.C.

(57) ABSTRACT

Methods for melanoma treatment and prevention with selective nitric oxide synthase inhibitor compounds and related pharmaceutical compositions, alone or in conjunction with one or more other melanoma therapies.

15 Claims, 18 Drawing Sheets

SPECIFIC NNOS INHIBITORS FOR THE THERAPY AND PREVENTION OF HUMAN MELANOMA

This application is a divisional of and claims prior benefit of application Ser. No. 13/348,819 filed Jan. 12, 2012 and issued as U.S. Pat. No. 8,642,282 on Feb. 4, 2014, and application Ser. No. 61/461,029 filed Jan. 12, 2011—each of which is incorporated herein by reference in its entirety.

This invention was made with government support under GM049725 awarded by the National Institutes of Health. The government has certain rights in the invention.

BACKGROUND OF THE INVENTION

Ultraviolet (UV) radiation has been implicated as a major environmental contributor to the development of most cutaneous melanomas. Sunscreens and sun awareness behavior have been used for the prevention of cutaneous melanoma, but their clinical utility remains mixed. The mechanistic role of UV radiation in melanomagenesis needs to be more comprehensively defined. However, it is known that in human skin, UV radiation not only generates reactive oxygen species (ROS), but also produces a marked increase of nitric oxide (NO). (Russo P. A., Halliday G. M. Inhibition of nitric oxide and reactive oxygen species production improves the ability of a sunscreen to protect from sunburn, immunosuppression and photocarcinogenesis. Br. J. Dermatol. 2006; 155:408-15). While the contributions of ROS to melanomagenesis have been extensively studied, characterizations of effects of NO stress and its detailed molecular mechanisms have been limited.

NO, produced from L-arginine by nitric oxide synthase (NOS), leads to highly reactive oxidants such as peroxynitrite, resulting in DNA damage even in physiologically relevant ranges of NO. In the skin, NO-mediated signaling also contributes to UV-induced melanogenesis and pigmentation. (Romero-Graillet C., Aberdam E., Clement M., Ortonne J. P., Ballotti R. Nitric oxide produced by ultraviolet-irradiated keratinocytes stimulates melanogenesis. J. Clin. Invest. 1997; 99:635-42.) Large quantities of NO have been detected in many types of cancer tissues, and the role of NO in carcinogenesis, tumor growth and metastasis has been well documented in skin cancer and other tumors. Constitutive production of NO in melanoma resulted in increased proliferation, impaired immune response, and lymphangiogenesis, associated with poor survival in patients. (Grimm E. A., Ellerhorst J., Tang C. H., Ekmekcioglu S. Constitutive intracellular production of iNOS and NO in human melanoma: possible role in regulation of growth and resistance to apoptosis. Nitric Oxide. 2008; 19:133-7; Massi D., De Nisi M. C., Franchi A., Mourmouras V., Baroni G., Panelos J., et al. Inducible nitric oxide synthase expression in melanoma: implications in lymphangiogenesis. Mod. Pathol. 2009; 22:21-30; Ekmekcioglu S., Ellerhorst J. A., Prieto V. G., Johnson M. M., Broemeling L. D., Grimm E. A. Tumor iNOS predicts poor survival for stage III melanoma patients. Int. J. Cancer. 2006; 119:861-6.)

The NOS family comprises inducible NOS (iNOS), endothelial NOS (eNOS), and neuronal NOS (nNOS), the latter of which is expressed mainly in neural tissue. Previous studies have largely focused on iNOS and its inhibitors, which exhibited promising chemopreventive activities in skin carcinogenesis but limited anti-melanoma potential. As melanocytes originate from the neural crest and have many gene expression characteristics similar to neural cells, nNOS may play a unique role in regulating NO levels in melanocytes. In contrast to iNOS-mediated generation of high levels of NO, nNOS produces lower levels of NO and mediates direct cellular effects such as neuromodulation. In a 1999 study, a progressive increase of nNOS expression was evident over the course of melanoma progression, suggesting that the de novo expression of nNOS may be a marker for an early stage of melanoma. (Ahmed B., Van Den Oord J. J. Expression of the neuronal isoform of nitric oxide synthase (nNOS) and its inhibitor, protein inhibitor of nNOS, in pigment cell lesions of the skin. Br. J. Dermatol. 1999; 141:12-9.) Differential expression of nNOS in tumorigenic and non-tumorigenic variants derived from the same melanoma cell line also has been reported. A recent clinical epidemiologic study investigated the role of polymorphisms of nNOS as related to outcome and demonstrated that certain nNOS (but not iNOS) genotypes were associated with an increased risk of cutaneous melanoma. (Li C., Hu Z., Liu Z., Wang L. E., Gershenwald J. E., Lee J. E., et al. Polymorphisms of the neuronal and inducible nitric oxide synthase genes and the risk of cutaneous melanoma: a case-control study. Cancer. 2007; 109:1570-8.) Moreover, this study also identified significant interactions of the combined nNOS genotypes and moles and the lifetime number of blistering sunburns.

With increasing evidence of the role of nNOS in melanoma progression, the art is likewise concerned with and directed to a search for specific nNOS inhibitors and related methods of melanoma treatment and prevention.

SUMMARY OF THE INVENTION

In light of the foregoing, it is an object of the present invention to provide one or more methods for the treatment and/or prevention of UV radiation-induced melanoma, thereby addressing various concerns relating to the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to extend inhibition of nitric oxide synthase inhibitors to the attenuation of cellular alterations induced by UV radiation.

It can be another object of the present invention to target neuronal nitric oxide synthase with one or more specific inhibitor compounds, including but not limited to those illustrated herein, to diminish nitric oxide stress in human melanoma.

It can be another object, alone or in conjunction with one or more of the preceding objectives, to provide one or more nNOS inhibitor compounds and/or related compositions to affect and/or inhibit induction of nNOS expression and/or melanoma cell proliferation.

Other objects, features, benefits and advantages of the present invention will be apparent from this summary and its descriptions of certain embodiments, and will be readily apparent to those skilled in the art of treatment and prevention of melanoma, related disease states and indications thereof. Such objects, features, benefits and advantages will be apparent from the above as taken into conjunction with the accompanying examples, data, figures and all reasonable inferences to be drawn therefrom, alone or with consideration of the references cited or incorporated herein.

In part, the present invention can be directed to a method for affecting and/or inhibiting a nitric oxide synthase. Such a method can comprise contacting, in vivo or in vitro, a human melanocyte or melanoma cell expressing nitric oxide synthase with an effective amount of a compound selected from compounds of a formula

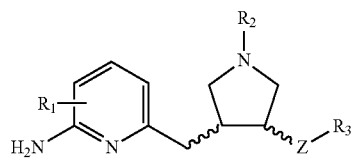

wherein $R_1$ can be selected from H, halogen, alkyl (e.g., $CH_3$), and substituted alkyl (e.g., $CF_3$) moieties; $R_2$ can be selected from H, alkyl, aryl, amino, hydroxy, substituted aryl or a substituted alkyl (e.g., but not limited to haloalkyl, arylalkyl, aminoalkyl or hydroxyalkyl) moieties; Z can be selected from NH, O, and NHCO; and $R_3$ can be selected from alkyl, substituted alkyl, hydroxyalkyl, substituted hydroxyalkyl, arylalkylaminoalkyl, substituted arylalkylaminoalkyl, arylalkyloxaalkyl, substituted arylalkyloxaalkyl, arylalkyl, substituted arylalkyl, arylalkylamidoalkyl (where the amido group is either NHCO or CONH), substituted arylalkylamidoalkyl, aminoalkyl, and substituted aminoalkyl moieties (e.g., but not limited to linear or cyclic alkylamine), where such substituents can include but are not limited to halogen (e.g., fluoro, chloro, etc.) substituent(s).

In certain embodiments, $R_1$ can be selected from H or various alkyl moieties. In a subset of such embodiments, $R_2$ can be H, and Z can be selected from NH and O with $R_3$ selected from phenylethyl (or phenylmethylene)aminoalkyl and substituted (e.g., without limitation fluoro-substituted) phenylethyl (or phenylmethylene)aminoalkyl moieties. In certain other embodiments, $R_1$ can be selected from H and methyl moieties, and $R_2$, $R_3$, Z and Y can independently vary as described elsewhere herein.

Such compounds are without stereochemical limitation. As illustrated below, such compounds and/or their intermediates are available as racemic mixtures from which isomers can be resolved or are diastereomers, from which cis and/or trans isomers can be separated. Accordingly, any stereocenter can be (S) or (R) with respect to any other stereocenter(s). Further, it will be understood by those skilled in the art that the compounds of this invention can comprise an acid salt, hydrate and/or solvate of any such compound. Without limitation, certain embodiments can be partially or fully protonated, comprising a primary, secondary and/or tertiary amine, whereby the counter ion(s) can be a conjugate base of a protic acid. Regardless, any such compound(s) can be provided as part of a pharmaceutical composition comprising a pharmaceutically-acceptable carrier component for use in conjunction with a method or medicament of this invention.

In part, the present invention can also be directed to a method of affecting, inhibiting and/or reducing NO production, such as can be induced by UV-radiation. Such a method can comprise contacting a cellular medium expressing or capable of expressing neuronal nitric oxide synthase with an effective amount of a selective inhibitor compound of the sort described herein, such as and without limitation compounds of a formula

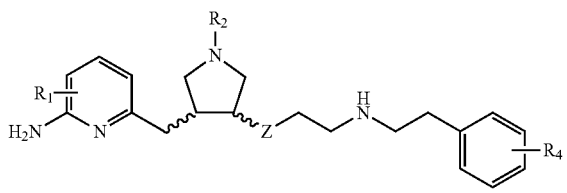

wherein $R_1$ can be selected from H, halogen, methyl and substituted methyl (e.g., fluoro substituted, etc.) moieties; $R_2$ can be selected from H, alkyl and substituted alkyl (e.g., fluoro-, amino-, etc.) moieties; Z can be selected from O and NH; and $R_4$ can be selected from H, alkyl, substituted alkyl (e.g., fluoro, chloro, etc.) and halogen (e.g., fluoro, chloro) moieties. Without limitation, the ethylaminoethyl and/or phenyl moieties can be substituted with one or more halo (e.g., fluoro and chloro), alkyl and/or haloalkyl (e.g., trifluoromethyl) substituents. Regardless, such a compound can be cis or trans with respect to the stereocenters and present as a salt, hydrate and/or solvate thereof.

In part, the present invention can also be directed to a method of affecting and/or inhibiting nNOS expression, such expression as can be induced by UV-radiation. Such a method can comprise providing a compound of the sort described above, such as and without limitation, of a formula

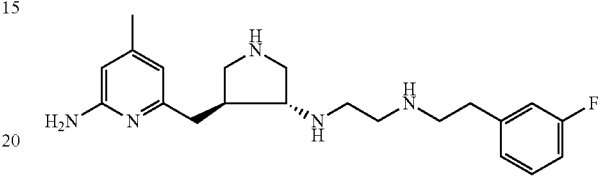

and contacting a cellular medium, expressing or capable of expressing neuronal nitric oxide synthase, with an effective amount of such a compound. The effect of such a compound on nNOS expression can be determined, as understood by those skilled in the art, through histological studies and immunoblotting assays of the sort described herein.

DETAILED DESCRIPTION OF CERTAIN EMBODIMENTS

Figure 1A:
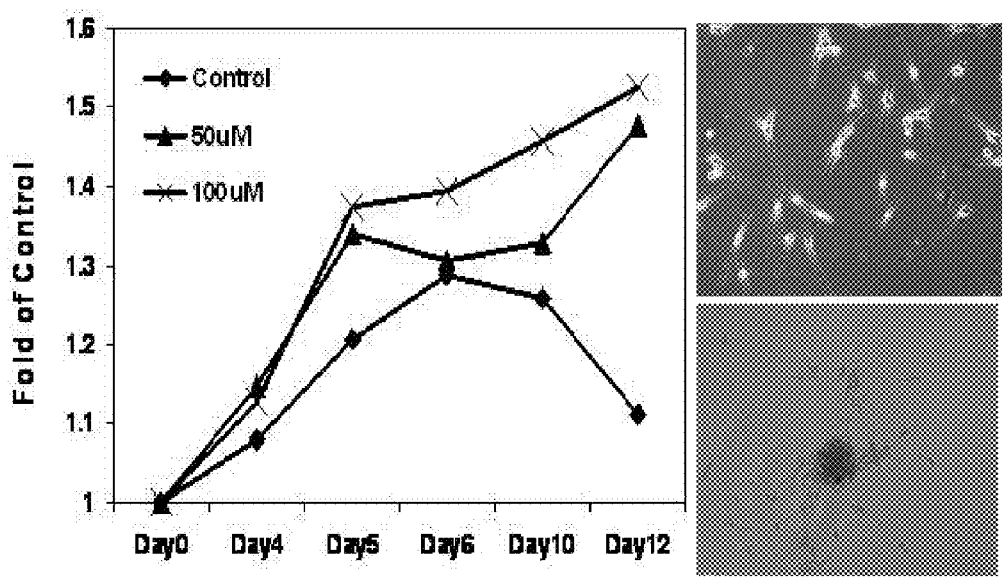
FIGS. 1A-D. (A) DETA/NO treatment stimulates melanocyte proliferation. The photos represent foci formed after 10 weeks. (B) NO stress generated by DETA/NO or L-arginine enhanced melanoma proliferation, more evident in metastatic cells. (C) Both UVA (3 $J/cm^2$) and UVB (25 $mJ/cm^2$) radiation increased NO levels in primary melanoma wm3211 cells. Results represent the means+/−SDs of three replicates. (D) Increased total NOS activities in melanoma cell lines compared to immortalized MEL-ST melanocytes. Results are expressed in folds of change standardized by Mel-ST cells for 3 biologic replicates. *, $p<0.05$ compared to Mel-ST cells.

By way of illustrating certain, non-limiting embodiments of this invention, correlations can be drawn with respect to nNOS/NO stress and melanoma progression. For instance, as demonstrated below, in human melanoma, nNOS expression is sensitive to UV radiation and associated with the increased generation of intracellular NO, which stimulates proliferation and invasion. Knockdown of nNOS reduced the metastatic capacity of melanoma, and similar inhibition was observed using novel, highly selective nNOS inhibitors. Representative studies relating to this invention show that targeting nNOS with specific inhibitors can be at least part of an effective strategy for the treatment of melanoma.

Initially, it was observed that iNOS is markedly induced after UV radiation and sunburn; that it plays an important role in carcinogenesis and skin tumor development has been well documented in many human and animal studies. In human melanoma, studies also demonstrated that iNOS expression was associated with poor survival and in predicting distance metastasis, and specific iNOS inhibitors were shown to inhibit melanoma growth. However, upon review of the specific iNOS inhibitors tested in these studies, it was noticed that these compounds actually were not so selective for iNOS inhibition. For example, the $K_{i(iNOS)}$ and $K_{i(nNOS)}$ value of 1,3-phenylene-bis(1,2-ethanediyl)bisisothiourea (PBIT) is 19 nM and 29 nM respectively, indicating the iNOS selectivity over nNOS is only 1.5 fold—suggesting that the reduction of melanoma growth caused by these compounds may not be due solely to iNOS blocking, but could also be related to nNOS inhibition.

Many chemopreventive agents from nutrients or diet, such as resveratrol and curcumin, exhibit potent inhibitory effects on NO generation. Specifically, modulation of iNOS expression has been observed in a wide range of in vitro and in vivo studies contributing to their chemopreventive activities. However, increased intracellular NO generation by L-arginine supplementation was not affected at all by either resveratrol or curcumin in melanoma cells, even up to a concentration of 50 μM. (See, e.g., example 5 and FIG. 5E, below.) Contrary thereto, nNOS inhibitor cpd 8, at concentrations as low as 1 μM, efficiently inhibited NO production in melanoma. Such results indicate that NO generation in melanoma is predominantly mediated by nNOS rather than iNos. (See, e.g., example 4 and FIGS. 4A-F, together with example 6 and FIGS. 6A-C, below.)

A study done with 41 benign nevi and 52 primary malignant melanomas showed that iNOS is expressed de novo in most benign pigment cell lesions, while it plays a less significant role in vertical growth phase and in metastatic melanoma. (Ahmed B., Van Den Oord J. J. Expression of the inducible isoform of nitric oxide synthase in pigment cell lesions of the skin. Br. J. Dermatol. 2000; 142:432-40.) By contrast, the present histological study of melanoma biopsies, there was a significant trend of nNOS staining increasing with disease stage. (See, e.g., example 2 and FIGS. 2A-D, below.) Such results suggest that nNOS staining may serve as an adjunct biomarker for melanoma diagnosis—and, that NO stress mediated by nNOS contributes more toward disease progression than serving as an initiating early event.

While there has been some disagreement regarding the relevant roles of UVA and UVB in melanomagenesis, the present data shows distinct effects of UVA and UVB on nNOS induction and NO generation, indicating that their regulatory mechanisms might be different. The large increases of nNOS expression induced by UVA lasted for at least 72 hours with significantly elevated intracellular NO production. (However, one literature study showed that in human keratinocytes, UVA-mediated NO formation was non-enzymatic and came from "NO-storage" in the skin, suggesting the induction of nNOS/NO by UVA might be of specific importance for melanoma cells.) In contrast to UVA, UVB-induced nNOS occurred in a transient, short-duration manner, and accordingly, the induction of NO was evident shortly after UVB and peaked at 4 hours, followed by a sharp drop. (See, e.g., example 1 and FIGS. 1A-D, below.) Although similar transient nNOS induction after UVB exposure was reported in HaCaT kerationcytes, the predominant elevation of NO levels was mediated by iNOS induction, especially in the late phase post-UVB (>6 hours). Such observations tend to suggest that the long-lasting nNOS induction by UVA might account for delayed chronic responses, and the transient nNOS induction by UVB might contribute to acute reactions.

L-Arginine is of particular importance in human melanoma. One reason is that L-Arginine serves as the substrate for overexpressed nNOS to generate NO in melanoma cells; another reason lies in the special amino acid metabolism that occurs in melanoma. Although in normal tissues arginine is not an essential amino acid, melanoma depends on an exogenous supply of arginine due to the lack of argininosuccinate synthetase (ASS). Currently, recombinant arginine deiminase, an Arg-degrading enzyme, is in Phase II clinical trials for metastatic melanoma patients. Relating to such developments, the present data shows that L-arginine significantly enhances the invasion potential of melanoma cells with increased NO production and stimulated melanoma overgrowth in 3-D skin reconstruct. Knockdown of nNOS (e.g., example 3, below) or utilization of specific nNOS inhibitors reversed the effects of L-arginine in melanoma, suggesting that the stimulating effects of L-arginine, at least in part, result from nNOS-mediated NO stress. (See, e.g., example 5 and FIGS. 5A-C, below.) Accordingly, in accordance with broader aspects of this invention, combination of L-arginine deprivation with nNOS inhibition may be used to achieve a better anti-melanoma efficacy.

Relating to the design of an inhibitor, NOS consists of a reductase domain, an oxygenase domain, and the substrate L-arginine. Although the 3 mammalian NOS isoforms (iNOS, nNOS, and eNOS) share approximately 50% amino acid identity, the crystal structures of the oxygenase domains (where substrate oxidation occurs) showed that the active sites are nearly identical. (Crane B. R., Arvai A. S., Gachhui R., Wu C., Ghosh D. K., Getzoff E. D., et al. The structure of nitric oxide synthase oxygenase domain and inhibitor complexes. Science. 1997; 278:425-31.) Until recently, isoform-selective drug design for NOS was a challenging problem. However, as illustrated below, the structural bases for a group of highly selective nNOS inhibitors have been successfully elucidated, leading to the design of more potent drug-like inhibitors. (See, e.g., Ji H., Li H., Martasek P., Roman L. J., Poulos T. L., Silverman R. B. Discovery of highly potent and selective inhibitors of neuronal nitric oxide synthase by fragment hopping. J. Med. Chem. 2009; 52:779-97; Silverman R. B. Design of selective neuronal nitric oxide synthase inhibitors for the prevention and treatment of neurodegenerative diseases. Acc. Chem. Res. 2009; 42:439-51; and Ji H., Tan S., Igarashi J., Li H., Derrick M., Martasek P., et al. Selective neuronal nitric oxide synthase inhibitors and the prevention of cerebral palsy. Ann. Neurol. 2009; 65:209-17.)

As shown through the present studies, potent nNOS inhibitors of the sort described herein—with distinct $K_i$ values for nNOS, iNOS and eNOS—efficiently inhibited UVA-induced NO production and reduced the invasion potential of metastatic melanoma cells. Comparison of their iNOS or nNOS inhibitory potency with observed anti-invasion activities found no significant correlations; however, a positive regression curve was more evident for nNOS, suggesting that the inhibitory effects of nNOS is more related to melanoma inhibition compared to that of iNOS and eNOS.

Accordingly, as demonstrated, targeting nNOS/NO with NOS inhibitors represents an innovative chemopreventive strategy. The high selectivity of the representative nNOS inhibitors described herein can be used to avoid off-target side effects of the sort that occur after administration of less-selective compounds. With such selective, bio-available and potent inhibitors, the present NO/nNOS-targeted methods can be used alone or in conjunction with one or more other melanoma therapies.

Compounds useful in conjunction with the present methods can be prepared, using synthetic techniques understood by those skilled in the art made aware of this invention. For instance,

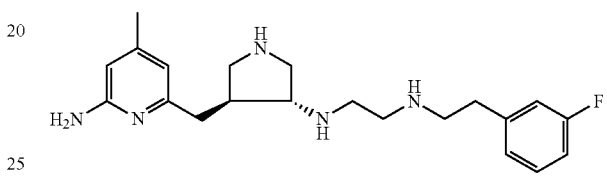

1 as shown in Scheme 1, the synthesis of inhibitor compound 1 (i.e., compound 8, FIG. 8) can begin with Boc-protected aminopyridine 2 (Delker, D. L.; Ji, H.; Li, H.; Jamal, J.; Fang, J.; Xue, X.; Silverman, R. B.; Poulos, T. L. Unexpected Binding Modes of Nitric Oxide Synthase Inhibitors Effective in the Prevention of Cerebral Palsy, *J. Am. Chem. Soc.* 2010, 132, 5437-5442.). Alkylheterocycle (e.g., a Boc-protected 2-aminopyridine) 3 is treated with two equivalents of n-BuLi, and the resulting dianion is allowed to react with a Boc-protected pyrrolidine epoxide (4) to generate the trans-alcohol (5a) in modest yields. The free NH group on the pyridine ring was further protected with a Bn-protecting group using NaH followed by BnBr to yield 6 in high yields. The stereochemistry of the hydroxyl carbon is inverted by a Mitsunobu reaction with HOAc (7), then hydrolysis gives (±)-8. The two enantiomers of 8 are resolved through camphanic ester derivatives using a Mitsunobu reaction to generate two separable diastereomers (9a and 9b) in excellent yields. Finally, the ester linkage of the desired diastereomer is hydrolyzed using $Na_2CO_3$ to provide chiral pyrrolidine precursor 10a in high yields.

Scheme 1. Synthesis of pyrrolidine precursor 10a

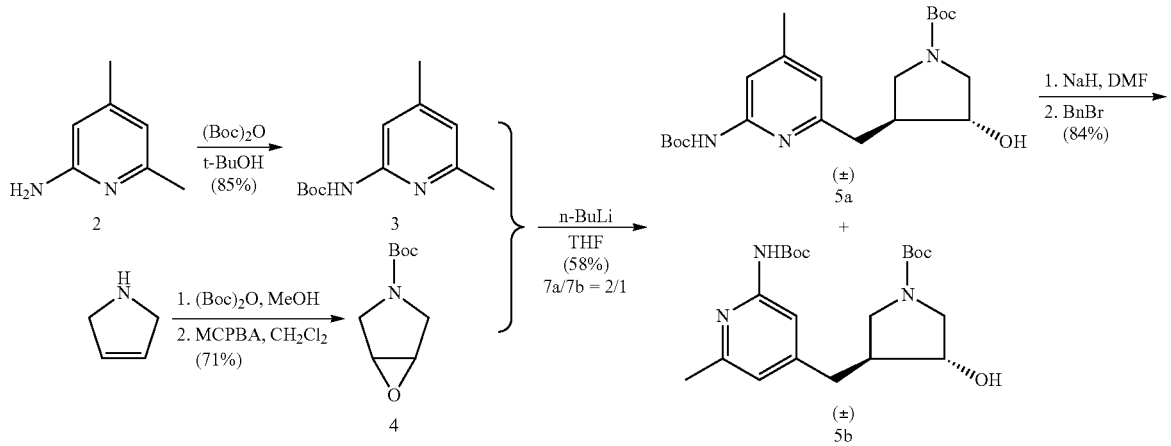

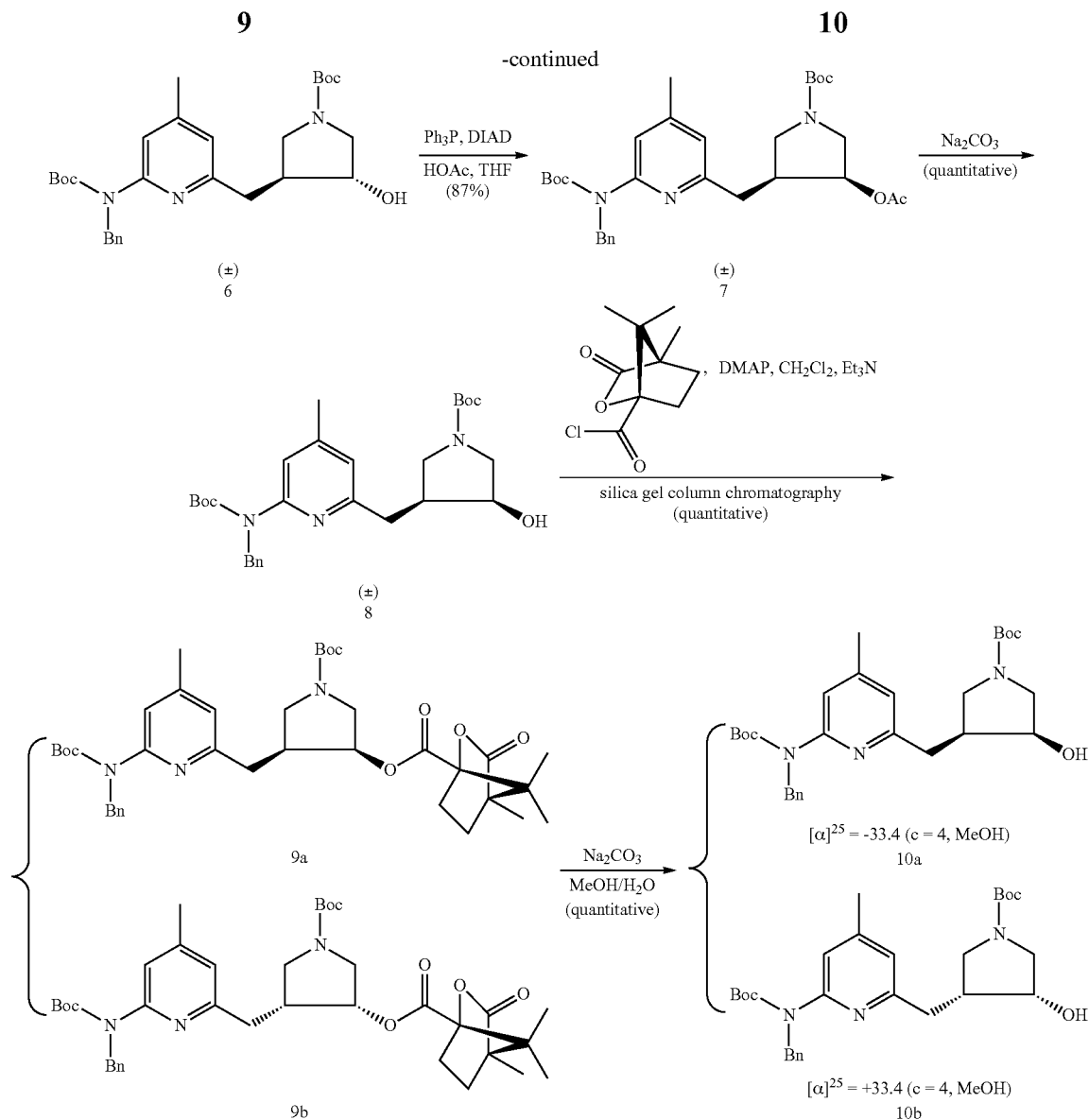

As shown in Scheme 2, chiral cis-alcohol 10a is treated under Mitsunobu conditions with DPPA to give trans azide 11. Simultaneous benzyl deprotection and azide reduction by palladium-catalyzed hydrogenolysis gives the corresponding chiral amine (12). Reductive amination with aldehyde 14 gives the triprotected 13. Deprotection with 4 N HCl in dioxane gives 1.

Scheme 2. Synthesis of compound 1

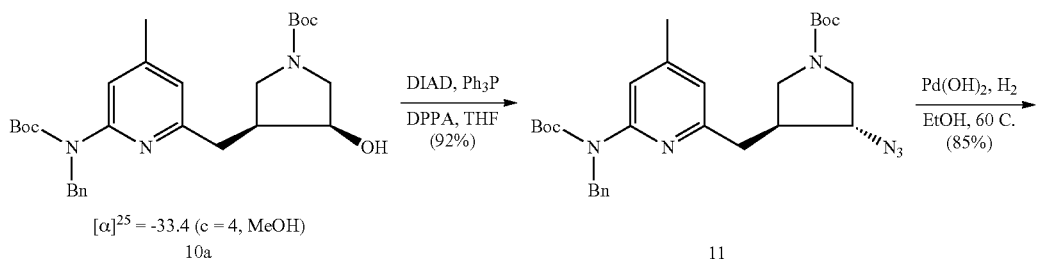

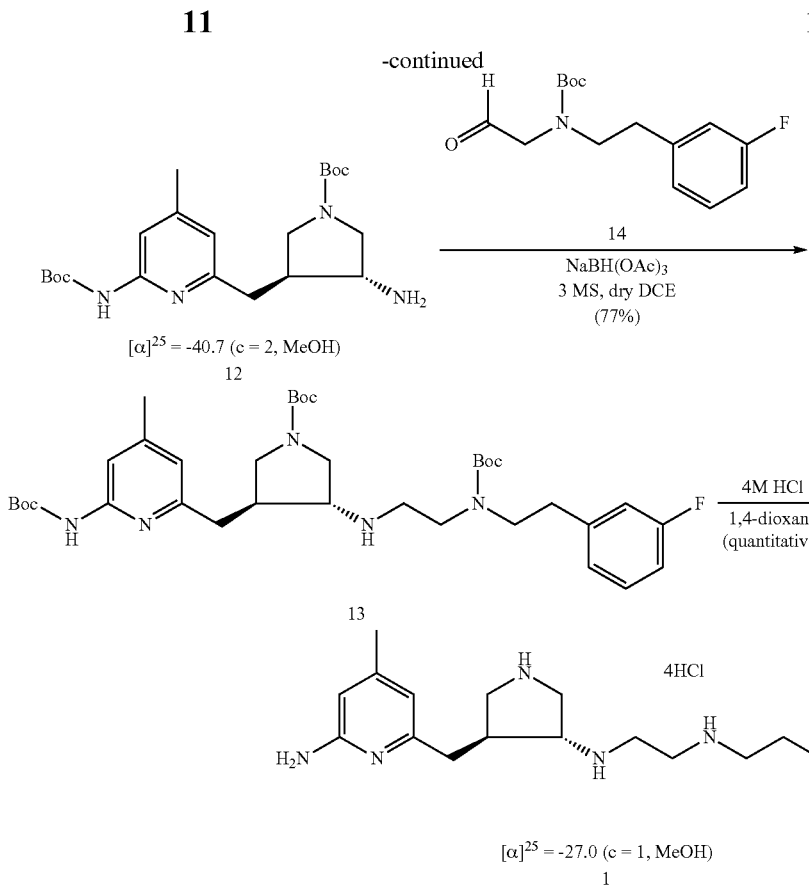

Aldehyde 14 can be prepared as shown in Scheme 3. 2-(3-Fluorophenyl)ethanol can be oxidized with Dess-Martin periodinane to give 15. Reductive amination with N-(2-hydroxyethyl)benzyl amine gives 16. Hydrogenolysis, Boc protection, and Dess-Martin oxidation gives 14 in excellent yields.

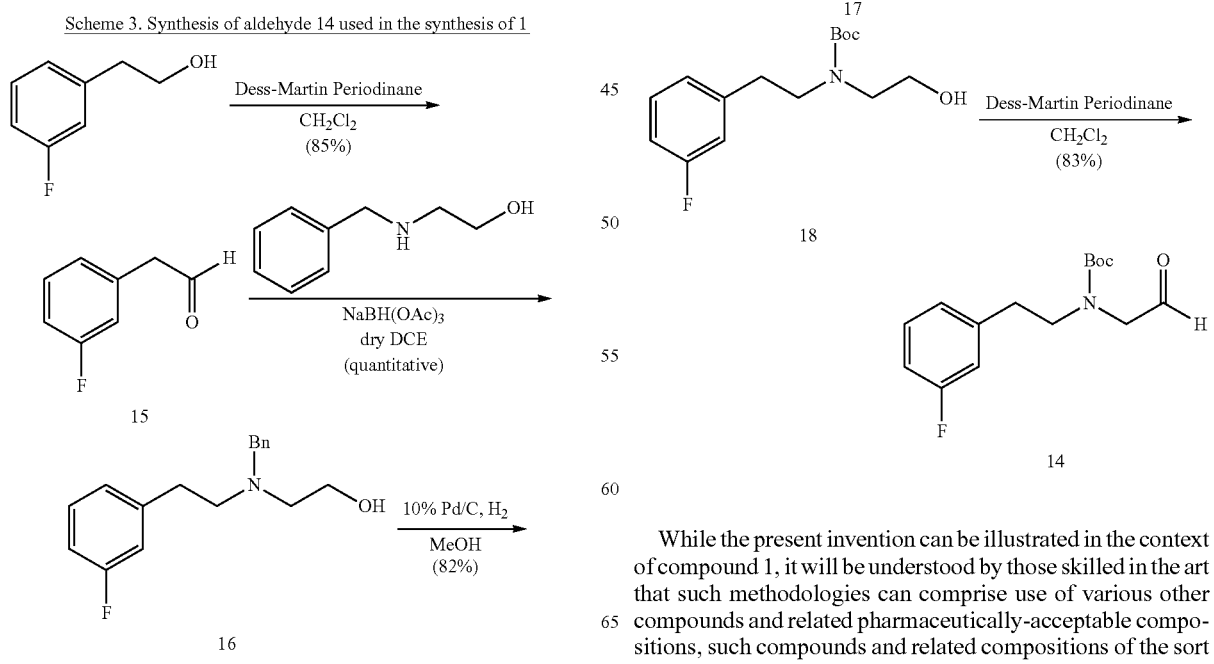

Figure 8:
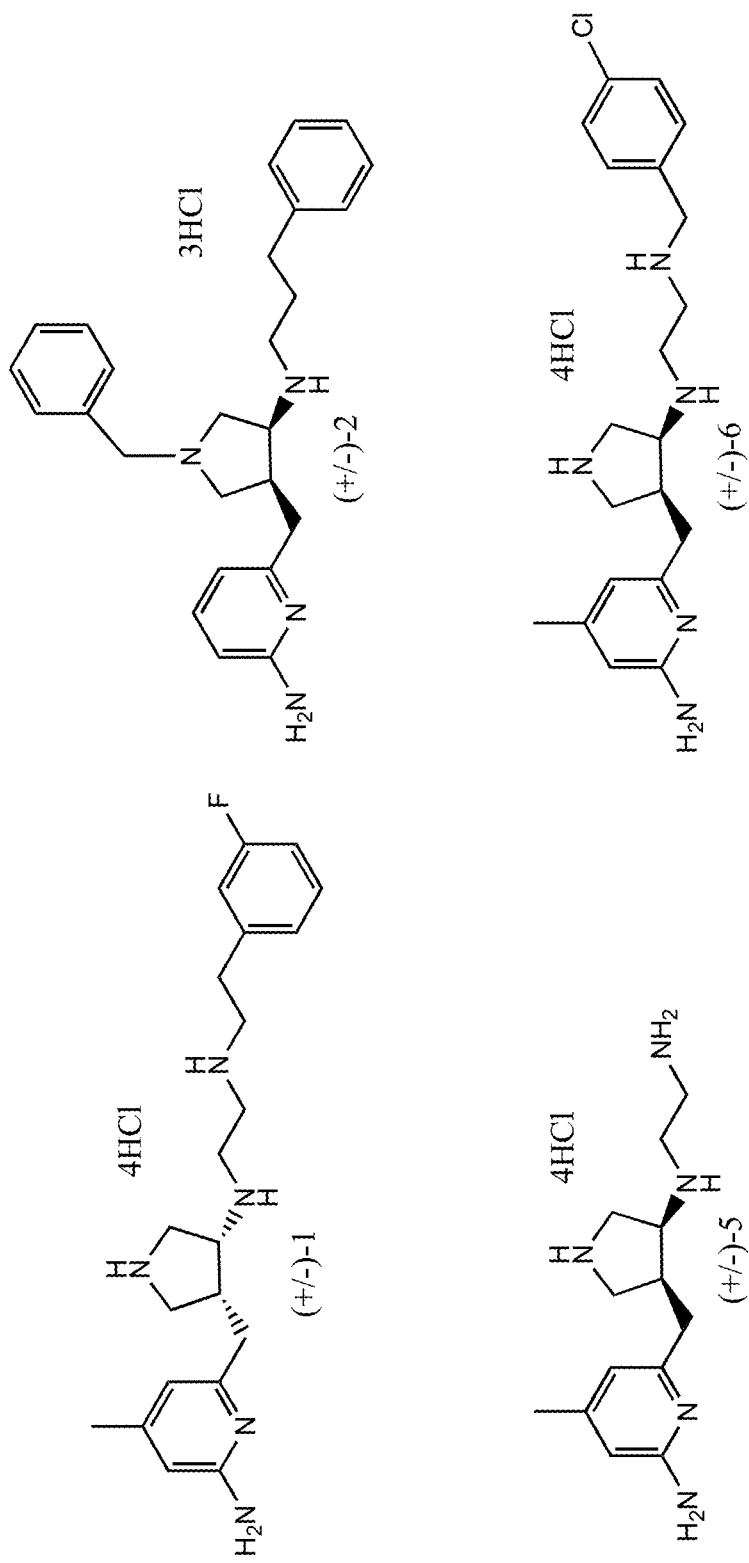
FIG. 8. Representative nNOS inhibitor compounds as can be used in accordance with one or more non-limiting embodiments of this invention.
Figure 8:
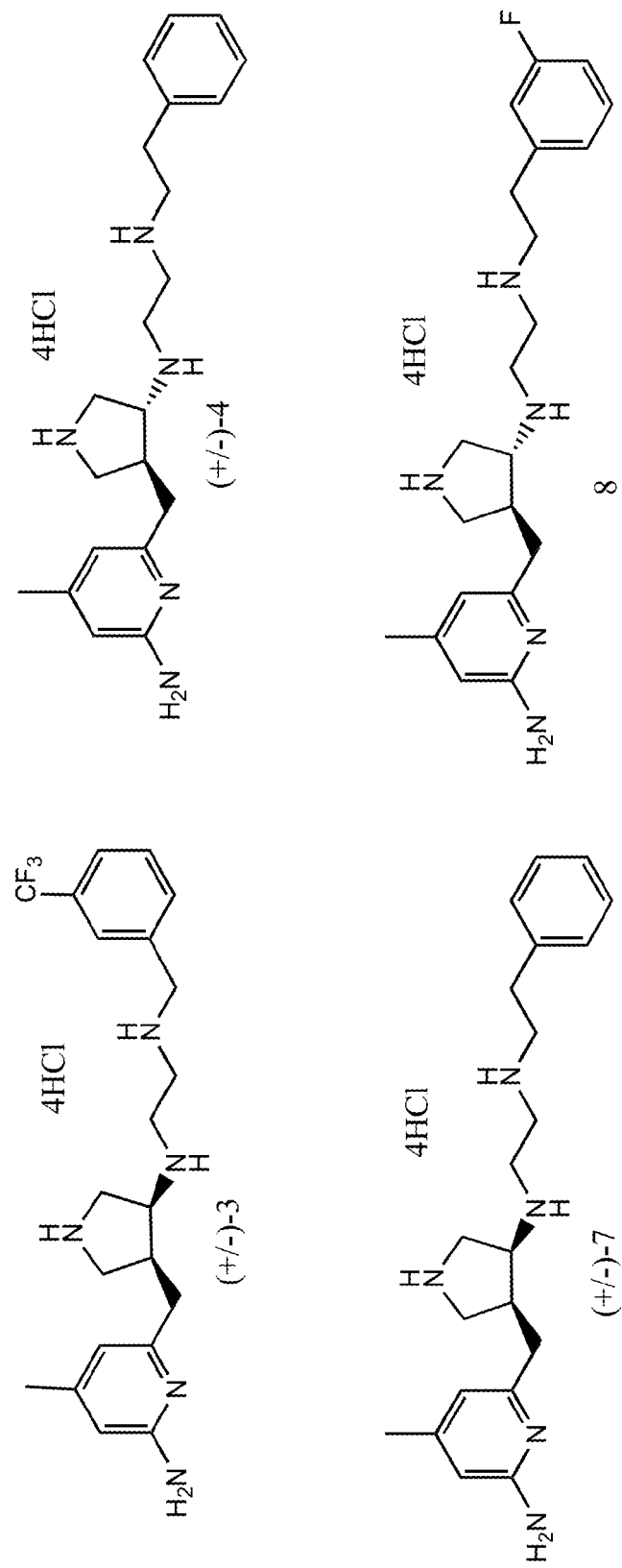

While the present invention can be illustrated in the context of compound 1, it will be understood by those skilled in the art that such methodologies can comprise use of various other compounds and related pharmaceutically-acceptable compositions, such compounds and related compositions of the sort described herein and available through the synthetic procedures described in U.S. Pat. Nos. 7,470,790 and 7,994,326—each of which is incorporated herein by reference in its entirety. Without limitation, a range of compounds varied by choice of Z and $R_3$ can be prepared as described in the context of substructure III, as discussed more fully in the incorporated references. Like, as discussed and illustrated in the aforementioned incorporated references, the ring moieties of substructures I and II can also be varied as discussed therein. Without limitation, several such compounds selective for inhibition of nNOS over the other isoforms and useful in conjunction with the present methodologies are shown in FIG. 8. Such compounds can be prepared using synthetic techniques of the sort illustrated above or in the incorporated references, or through straight-forward modifications of such synthetic techniques—such modifications as would also be understood by those skilled in the art and made aware of this invention—and are limited only by commercial or synthetic availability of suitable starting materials and reagents.

With reference to FIG. 8 (and Table 1, below) representative compounds useful in conjunction with the present methods include but are not limited to:

$N^1$-((3R,4R)-4-((6-amino-4-methylpyridin-2-yl)methyl)pyrrolidin-3-yl)-$N^2$-(3-fluorophenethyl)ethane-1,2-diamine (1);

6-(((3S,4S)-1-benzyl-4-((3-phenylpropyl)amino)pyrrolidin-3-yl)methyl)pyridin-2-amine (2);

$N^1$-((3S,4S)-4-((6-amino-4-methylpyridin-2-yl)methyl)pyrrolidin-3-yl)-$N^2$-(3-(trifluoromethyl)benzyl)ethane-1,2-diamine (3);

$N^1$-((3R,4S)-4-((6-amino-4-methylpyridin-2-yl)methyl)pyrrolidin-3-yl)-$N^2$-phenethylethane-1,2-diamine (4);

$N^1$-((3S,4S)-4-((6-amino-4-methylpyridin-2-yl)methyl)pyrrolidin-3-yl)ethane-1,2-diamine (5);

$N^1$-((3S,4S)-4-((6-amino-4-methylpyridin-2-yl)methyl)pyrrolidin-3-yl)-$N^2$-(4-chlorobenzyl)ethane-1,2-diamine (6);

$N^1$-((3S,4S)-4-((6-amino-4-methylpyridin-2-yl)methyl)pyrrolidin-3-yl)-$N^2$-phenethylethane-1,2-diamine (7); and $N^1$-((3R,4S)-4-((6-amino-4-methylpyridin-2-yl)methyl)pyrrolidin-3-yl)-$N^2$-(3-fluorophenethyl)ethane-1,2-diamine (8). (Nomenclature for such compounds provided using ChemBioDraw Ultra, version 12.0.2.1076.)

Methods of the present invention can also, as would be understood by those skilled in the art, be extended to or include methods using or in conjunction with a pharmaceutical composition comprising an inhibitor compound of the sort described herein and a physiologically or otherwise suitable formulation. In a some embodiments, the present invention includes one or more NOS inhibitors, as set forth above, formulated into compositions together with one or more physiologically tolerable or acceptable diluents, carriers, adjuvants or vehicles that are collectively referred to herein as carriers. Compositions suitable for such contact or administration can comprise physiologically acceptable sterile aqueous or nonaqueous solutions, dispersions, suspensions or emulsions. The resulting compositions can be, in conjunction with the various methods described herein, for administration or contact with a human/animal melanocyte, melanoma cell and/or a nitric oxide synthase expressed or otherwise present therein. Whether or not in conjunction with a pharmaceutical composition, "contacting" means that a nitric oxide synthase and one or more inhibitor compounds are brought together for purpose of binding and/or complexing such an inhibitor compound to the enzyme. Amounts of a compound effective to inhibit a nitric oxide synthase may be determined empirically, and making such determinations is within the skill in the art. Inhibition or otherwise affecting nitric oxide synthase activity includes both reduction and/or mitigation, as well as elimination of NOS activity and/or nitric oxide production.

It is understood by those skilled in the art that dosage amount will vary with the activity of a particular inhibitor compound, disease state, route of administration, duration of treatment, and like factors well-known in the medical and pharmaceutical arts. In general, a suitable dose will be an amount which is the lowest dose effective to produce a therapeutic or prophylactic effect. If desired, an effective dose of such a compound, pharmaceutically-acceptable salt thereof, or related composition may be administered in two or more sub-doses, administered separately over an appropriate period of time.

Methods of preparing pharmaceutical formulations or compositions include the step of bringing an inhibitor compound into association with a carrier and, optionally, one or more additional adjuvants or ingredients. For example, standard pharmaceutical formulation techniques can be employed, such as those described in Remington's Pharmaceutical Sciences, Mack Publishing Company, Easton, Pa.

Regardless of composition or formulation, those skilled in the art will recognize various avenues for medicament administration, together with corresponding factors and parameters to be considered in rendering such a medicament suitable for administration. Accordingly, with respect to one or more non-limiting embodiments, the present invention provides for use of one or more neuronal nitric oxide synthase inhibitor compounds for the manufacture of a medicament for therapeutic use in the treatment of human melanoma or the prevention thereof.

EXAMPLES OF THE INVENTION

The following non-limiting examples and data illustrate various aspects and features relating to the methods of the present invention, including the use and administration of various nitric oxide synthase inhibitor compounds, as are available through the synthetic methodologies described herein. In comparison with the prior art, the present methods provide results and data which are surprising, unexpected and contrary thereto. While the utility of this invention is illustrated through the use of several inhibitor compounds and related pharmaceutical compositions, it will be understood by those skilled in the art that comparable results are obtainable with various other inhibitor compounds and compositions, as are commensurate with the scope of this invention.

Materials and Methods

Cell Culture: Human melanocytes were isolated from newborn foreskin following the procedure described previously, and cultured in MCDB153 medium (Sigma, St. Louis, Mo.). (Yang S., Irani K., Heffron S. E., Jurnak F., Meyskens F. L., Jr. Alterations in the expression of the apurinic/apyrimidinic endonuclease-1/redox factor-1 (APE/Ref-1) in human melanoma and identification of the therapeutic potential of resveratrol as an APE/Ref-1 inhibitor. Mol. Cancer Ther. 2005; 4:1923-35.) Primary fibroblast cells and keratinocytes were also isolated from foreskins according to literature procedures, and cultured in DMEM medium and EpiLife medium respectively (<10 passage).

Primary melanoma wm3211 cells were cultured in RPMI1640 with 10% fetal bovine serum (FBS), pennicillin (100 units/ml)/streptomycin (0.1 mg/ml), and 0.01 mg/mL insulin. Human metastatic melanoma cell line Lu1205 was cultured in L15/MCDB medium with 10% FBS and pennicillin/streptomycin. Human metastatic melanoma A375 (ATCC), SK-Mel28 (ATCC), c83-2c, c81-61 and c81-46A cells were cultured in DMEM or F10 medium respectively;

each supplied with 5% FBS, 5% new born bovine serum, and penicillin and streptomycin (Yang, supra).

Mouse melanocytes (Melan-A) were cultured in RPMI1640 medium supplied with 10% FBS, pennicillin/streptomycin, 0.1 mM 2-mercaptoethanol, and 200 nM TPA. Mouse melanoma cells F5061, F4280b and F5127 were established in melanoma lesions developed in HGF/SF transgenic mouse and were cultured in DMEM medium with 10% FBS, penicillin/streptomycin.

Reagents and Antibodies: The NO donor DETA/NO (Alexis Biochemicals.) was dissolved in PBS and used at a concentration of 100 µM. Resveratrol and curcumin were purchased from Sigma Life Sciences, dissolved in DMSO, and used at a concentration of 50 µM. L-arginine was also ordered from Sigma and the final concentration used in this study is 2.87 mM. The following primary antibodies were used for Immunoblotting analysis: JunD, MMP-1, Bcl-2, S-100, and nNOS (SC-17825) were from Santa Cruz Biotechnology; α-tubulin or β-actin antibody was from Sigma Life Sciences; and APE/Ref-1 antibody was from Novus Biologicals. HRP-conjugated anti-mouse and anti-rabbit antibodies were from Santa Cruz Biotechnology.

Proliferation analysis: MTT Colorimetric Assay was utilized for cell proliferation analysis according to manufacturer's protocol (Vybrant®, Molecular Probes, Inc. Eugene, Oreg.).

Tissue array and IHC staining. A human melanoma tissue array (ME482) was purchased from U.S. Biomax, Inc. The tissue array includes matched normal skin tissues, which were biopsied from the adjacent tissue of each cancer tissue from individual patients. The HRP-AEC Chromogen staining kit (R&D Systems) was used to visualize the expression levels of nNOS. Briefly, the slide was deparaffinized and rehydrated through a graded series of ethanol. After sequential blockings with Peroxidase/Serum/Avidin/Biotin Blocking reagents, the slide was incubated with nNOS antibody (1:500) at 4° C. overnight. Following washes, the secondary biotinylated anti-mouse antibody (1:200) and HSS-HRP were sequentially applied for 30 min at room temperature, and reaction product was visualized with hydrogen peroxide and AEC as chromogenic substrate, which revealed a bright red immunoreactivity. All the samples were counterstained by Haematoxylin.

Cell Protein Extraction and Western Blot Analysis: Melanoma cells were collected and lysed as described previously. (Yang Z., Yang S., Misner B. J., Chiu R., Liu F., Meyskens F. L., Jr. Nitric oxide initiates progression of human melanoma via a feedback loop mediated by apurinic/apyrimidinic endonuclease-1/redox factor-1, which is inhibited by resveratrol. Mol. Cancer Ther. 2008; 7:3751-60.) Equal amounts of protein samples were subjected to SDS-PAGE, and transferred to nitrocellulose membranes. The specific protein was then detected by the antibodies [anti-APE/Ref-1 (1:3500), anti-nNOS, anti-Bcl-2 and anti-MMP-1 (1:1000), anti-AP-1/JunD and anti-α-Tubulin or anti-actin (1:1,000)] followed by a chemiluminescence detection reagent (Peirce). Measurement of signal intensity on membranes was done using an imaging densitometer with Multi-Analyst software (Bio-Rad). All data were expressed as fold change of the control based on the calculation of density values of the specific protein bands standardized by α-Tubulin/actin.

Measurements of intracellular Nitric Oxide levels and NOS activities: NO was measured as nitrite by interaction with Griess reagent (Enzo Life Sciences, Lausen, Switzerland). The absorbance at 548 nm was detected and converted to nitrite concentrations according to the standard curve. The NOS activity was analyzed by Ultrasensitive Colorimetric Assay according to manufacturer's protocol (Oxford Biomedical Research, Inc., Oxford, Mich.).

UV radiation and cell treatment: Cells were grown to about 70% confluence and media was removed completely for UV radiation. For UVA radiation, 5 ml of PBS was added to one 10-cm dish of cells and ice cubes were placed next to dishes for absorbing the heat generated by UVA. UVA or UVB radiation was performed in a Stratagen crosslinker with peak wavelength at 350 nm or 312 nm respectively. The UV intensity was measured by a radiometer with proper probes. Fresh media was added back after radiation and cells were returned to 37° C. incubator for recovering. For drug treatments, nNOS inhibitors or resveratrol or curcumin were added into culture media either 24 hr before radiation or right after radiation when adding fresh media.

Invasion Assay: The invasiveness of melanoma cells was assessed on the basis of invasion of cells through Matrigel-coated membrane (BD Biosciences). Briefly, melanoma cells were collected and reconstituted in serum-free medium. Prepared cells were added to the upper Matrigel-coated insert. After 20 hr incubation, cells were fixed and stained with hematoxylin. Membranes were visualized microscopically and the invading cells on each of triplicate membranes were counted and averaged for 20 random fields.

Transient Transfection Studies: Small interfering RNA (siRNA) duplexes directed against NOS1 (nNOS) were purchased directly from Sigma-Aldrich (NM_000620). $1 \times 10^5$ cells were seeded in a 6-well plate. After 24 hours, the cells were transfected with nNOS siRNA or control siRNA to give the final concentration of 60 nmol/L according to the manufacturer's directions via Lipofectamine (Invitrogen, Inc.). Thirty hours later, cells were treated with L-arginine.

3-Dimensional Skin Reconstructs: A 3-dimensional skin reconstruct was achieved using a literature method. (Herlyn M., Hsu M. Y., Meier F. E., Nesbit M., Hsu J. Y., Van Belle P., et al. E-cadherin expression in melanoma cells restores keratinocyte-mediated growth control and down-regulates expression of invasion-related adhesion receptors. American Journal of Pathology. 2000; 156:1515-25.) Epidermal equivalents were constructed by mixing metastatic melanoma A375 cells with keratinocytes at ratio of 1:15. Once the epidermus is adhered to the dermal layer, skin equivalents are then lifted to the air liquid interface to allow keratinocytes differentiation. In term of treatments, L-arginine (2.87 mM) in absence or presence of nNOS inhibitor cpd 8 (a/k/a JI-11) was added directly to the culture medium from the lift-up day for 2 weeks. By the end of experiments, the skin equivalents were fixed and stained with H&E for pathological evaluation. S-100 staining as a melanocyte biomarker was performed to visualize and confirm the lesion of melanoma.

Synthesis of novel nNOS inhibitors and the docking model: The design and syntheses of nNOS inhibitors useful in conjunction with this invention have been reported previously. (See, e.g., Ji H., Delker S. L., Li H., Martasek P., Roman L. J., Poulos T. L., et al. Exploration of the active site of neuronal nitric oxide synthase by the design and synthesis of pyrrolidinomethyl 2-aminopyridine derivatives. J. Med. Chem. 2010; 53:7804-24; and Ji H., Li H., Martasek P., Roman L. J., Poulos T. L., Silverman R. B. Discovery of highly potent and selective inhibitors of neuronal nitric oxide synthase by fragment hopping. J. Med. Chem. 2009; 52:779-97.) Among them, without limitation, 8 representative compounds were utilized to illustrate a varied range of structures and related activities (summarized in Table 1, below).

Ki value calculation: Recombinant NOS isozymes overexpressed in *E. coli* were utilized. (Ji, H., et al., Discovery of highly potent and selective inhibitors of neuronal nitric oxide synthase by fragment hopping. J. Med. Chem., 2009. 52(3): p. 779-97; Ji, H., et al., Exploration of the active site of neuronal nitric oxide synthase by the design and synthesis of pyrrolidinomethyl 2-aminopyridine derivatives. J. Med. Chem., 2010. 53(21): p. 7804-24.) Relative enzyme inhibition activity [%] vs. Log (inhibitor concentration [M]) correlation was analyzed by Prism using nonlinear regression method to generate $IC_{50}$ value. The $K_i$ value was calculated by $IC_{50}=K_i(1+[S]/K_m)$.

Adhesion analysis of human metastatic melanoma A375 cells to fibroblast cells: A375 cells were added to fibroblast cell monolayer (FB) and incubated with presence or absence of nNOS inhibitors for 1 hour. Non-adhesive cells were washed away by PBS and MTT reagent was utilized to determine the relative amount of cells that adhered to FB cells, which is calculated as: relative adhesive cell OD value= (sample OD value (adhesive melanoma cells+FB)−negative control OD value (FB only)). The mean changes of OD values with treatments (control is set as 0) represented the relative effects of compounds on melanoma adhesion.

Statistical Analysis: Data are presented as the mean±SD from three independent experiments. Student's t test was used to compare two groups, with a P value of <0.05 considered statistically significant. All tests were two sided. One-way ANOVA was performed to study the association between the nNOS staining scores and disease stages, followed by linear trend analysis. Linear regression analysis was applied to study the association between nNOS/iNOS inhibition and anti-invasion activities of novel synthesized inhibitors. The coefficient of determination ($R^2$) and the p-value were reported.

Example 1

Figure 1B:
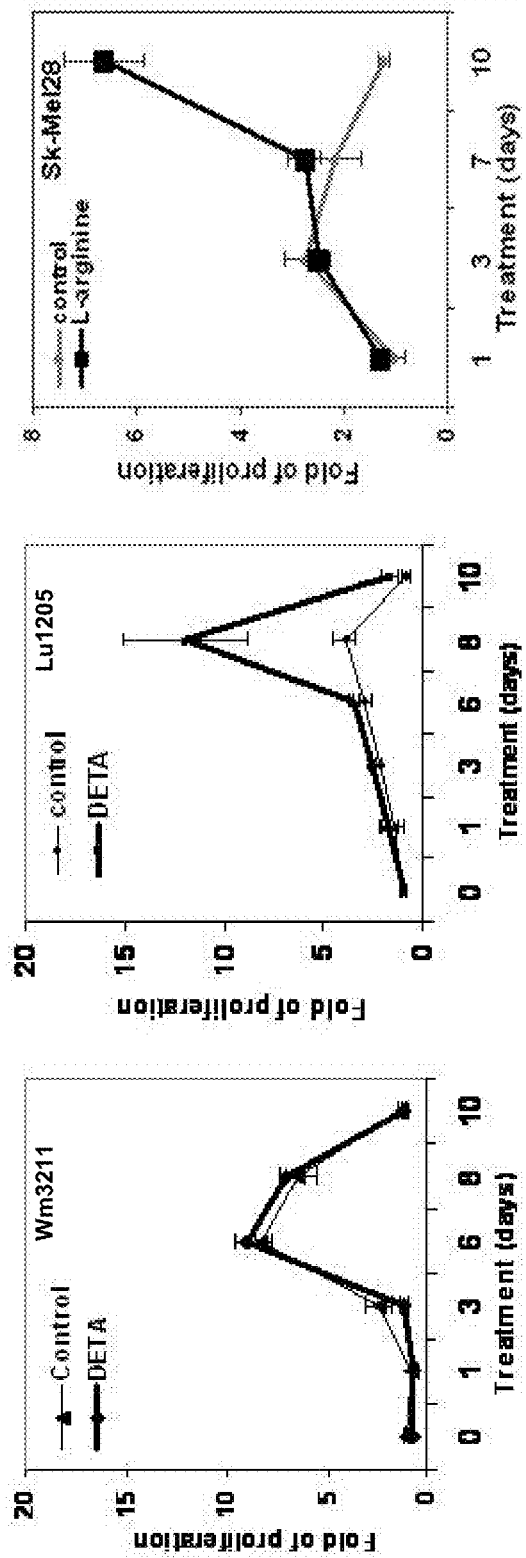
Figure 1C:
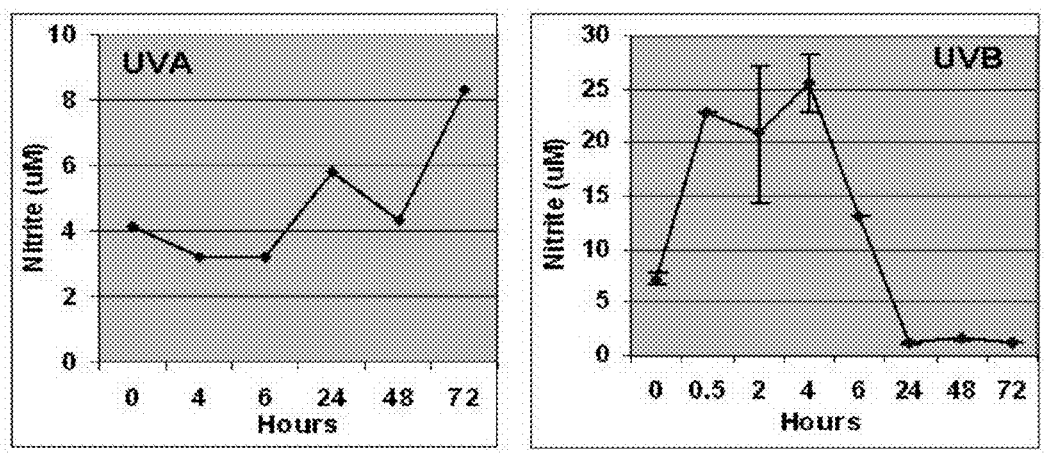

NO stress stimulates the proliferation of melanoma cells in vitro. NO donor DETA/NO (1-[N-(2-Aminoethyl)-N-(2-ammonioethyl)amino]diazen-1-ium-1,2-diolate)was utilized to mimic NO stress in cell culture media. As shown in FIG. 1A, in human primary melanocytes, cell proliferation measured by the MTT colorimetric assay in a 12-day period was significantly stimulated by DETA/NO exposure compared to control. At the end of the experiment, melanocytes incubated with DETA/NO were still proliferative, while the proliferation of control cells peaked by day 6 and started to drop. When extending the exposure time of DETA/NO in melanocytes to 10 weeks, it was observed that many foci formed in culture dishes and cells exhibited notable vertical growth potential: these foci were sub-cloned and re-seeded in a low density and showed evidence of continued foci formation. Marked stimulation of proliferation was also evident in human metastatic Lu1205 and SK-Mel28 cells with DETA/NO (100 µM) treatment (FIG. 1B). However, such increases were not significant in primary melanoma wm3211 cells.

To explore the effects of UV radiation on NO generation, primary melanoma wm3211 cells were irradiated with UVA (3 J/cm$^2$) or UVB (25 mJ/cm$^2$) respectively, and whole cell lysates were collected at different time points. The intracellular NO levels detected by the Griess reagent were both significantly elevated (FIG. 1C); however, the pattern of induction was different after UVA and UVB. UVB-induced NO generation was rapid (30 minutes), potent, peaked by 4 hours and was gone by 24 hours, while the increase of NO by UVA radiation was not evident until after 24 hours and lasted for at least 72 hours.

Figure 1D:
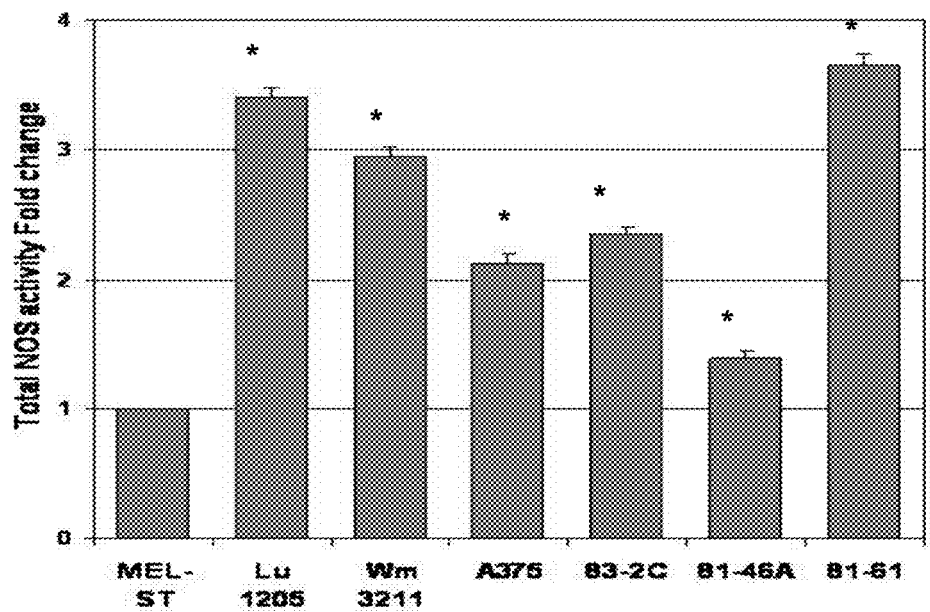

Employing the Ultrasensitive Colorimetric NOS Assay, it was demonstrated that compared to immortalized melanocytes (Mel-ST cells) all tested human melanoma cell lines exhibited a marked elevation of total NOS activities, although no correlations was evident with the metastasis status of tested cell lines (FIG. 1D).

Figure 2A:
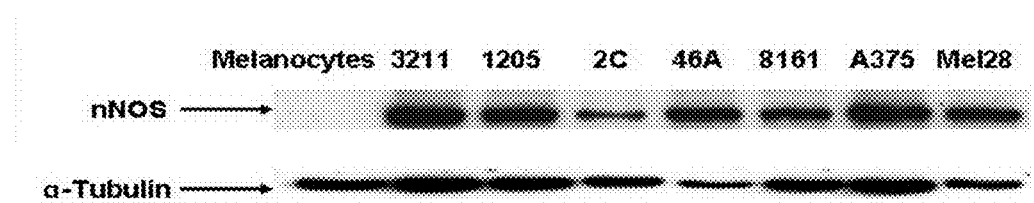
FIGS. 2A-H. nNOS expression is elevated in melanoma compared to normal melanocytes. (A) Immunoblotting assay of human primary melanocytes and melanoma cell lines; (B) Immunoblotting assay of mouse melanoma cell lines (F4280B, F5061 and F5127) and mouse melanocytes (MMC). (C) Immunohistochemistry analysis of nNOS expression levels using melanoma tissue array. Positive cells were visualized by light microscope and at least 10 highlight fields of each sample were examined. (D) Increased nNOS stainings in melanoma biopsies were significantly correlated with disease stages. IHC staining score was determined by the average percentage of cells positive for nNOS: 0, 0-5%; 1, 6-30%; 2, 31-59%; 3, >60%. The number of samples in normal, T2N0M0, T3N0M0 and T4N0M0 were 23, 3, 9 and 10 respectively. *, $p<0.05$ compared to normal skin tissue. (E-F) nNOS expression is markedly increased by UVA (D) or UVB (E) radiation in human melanoma cells. The represented data was done in wm3211 cells. (G-H) bFGF (10 ng/ml) treatment induced nNOS expression in normal Caucasian melanocytes, but DETA/NO and UVB produced no increase of nNOS levels.
Figure 2B:
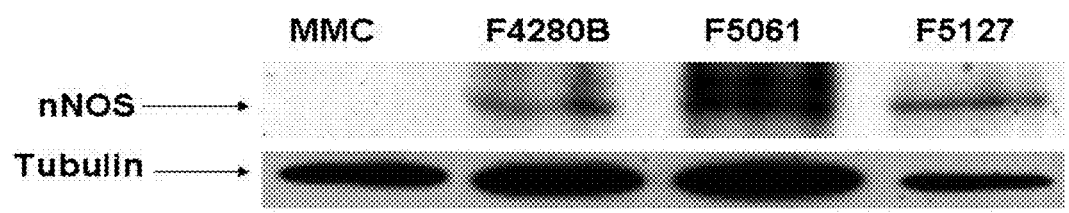
Figure 2C:
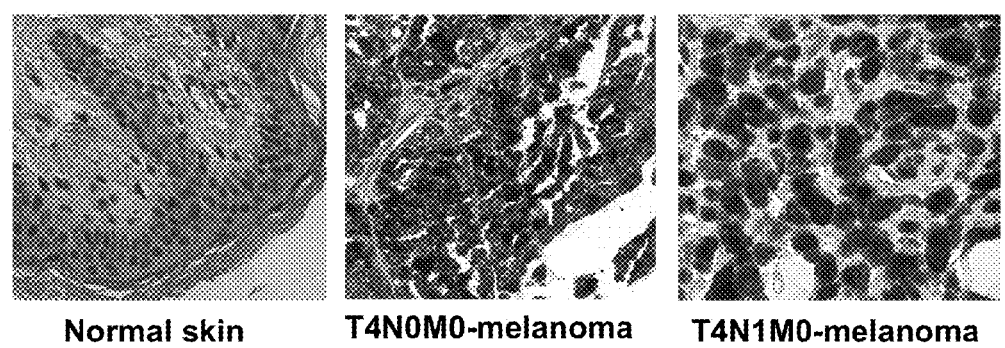

Example 2 nNOS expression is elevated melanoma compared to normal melanocytes, which is sensitive to UV radiation and growth factors. First, as shown in FIG. 2A, an immunoblotting assay revealed that the nNOS expression levels in human melanoma cell lines were much higher compared to levels in primary normal human melanocytes. Similar experiments were also carried out with mouse cells since UVB-induced melanoma in the HGF/SF transgenic mouse melanoma model is well characterized and recapitulates fairly well the etiology and histopathology of human melanoma. (Noonan F. P., Otsuka T., Bang S., Anver M. R., Merlino G. Accelerated ultraviolet radiation-induced carcinogenesis in hepatocyte growth factor/scatter factor transgenic mice. Cancer Res. 2000; 60:3738-43.) Three mouse melanoma cell lines established from the developed lesions have been used as the screening panel for translational or mechanistic studies. Similar to human cells, immunoblotting study also showed marked elevated nNOS expressions compared to normal mouse melanocytes in vitro, especially in F5061 cells, which are aggressively tumorigenic and metastatic (FIG. 2B).

Figure 2D:
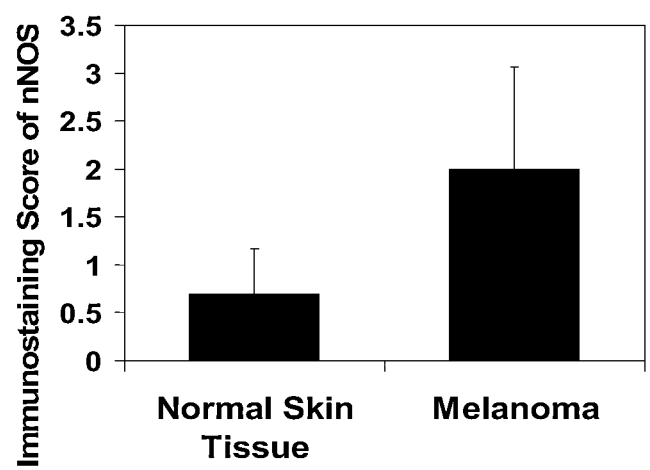
Figure 2D:
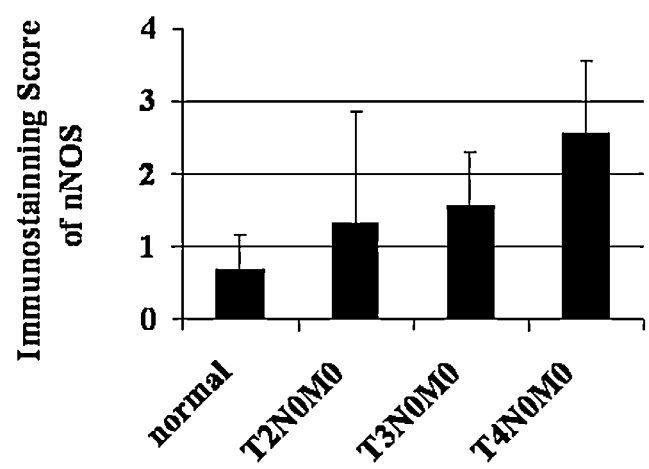

Consistent with what was found in vitro, histologic examination and IHC staining revealed that nNOS levels detected in melanoma biopsies were much higher than that of adjacent normal skin, and the average staining score of pooled melanoma samples were increased by 1.9 fold (FIG. 2D, p<0.05). When grouping melanoma samples based on disease stage, a trend of increased nNOS staining scores was observed with melanoma progression in patient biopsies (Trend analysis, p<0.0001, FIG. 1D). The average score of T4N0M0 samples was 2.56, ~2 fold of that of T2N0M0 ones (1.33).

Figure 2E:
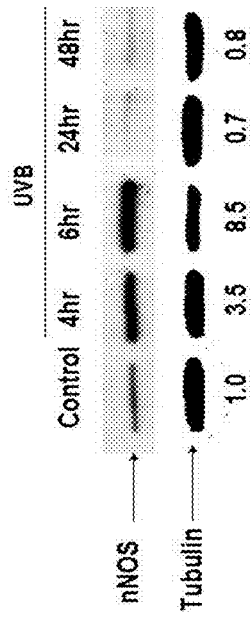

Given that UV radiation induced a marked increase in NO levels, the effects of UV irradiation on nNOS expression were investigated. Notably, both UVA and UVB treatments efficiently induced the expression of nNOS protein, but in different time-related patterns (FIG. 2D-E). The induction of nNOS by UVA lasts much longer (for at least 3 days), while UVB-induced nNOS peaked by 6 hours and diminished quickly. Such distinct patterns coincided with NO level changes after UVA or UVB irradiation, indicating the direct involvement of nNOS in UV-induced NO production in melanoma cells.

Figure 2F:
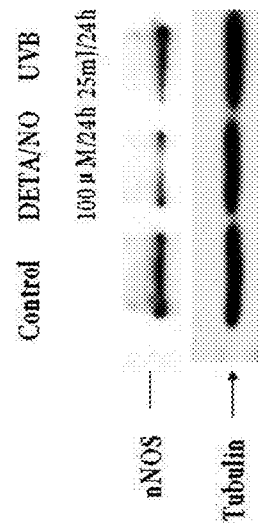
Figure 2G:
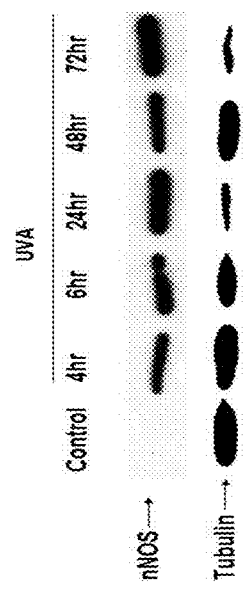
Figure 2H:
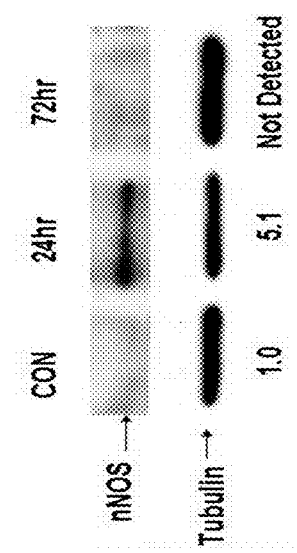

Interestingly, in normal melanocytes, growth factor bFGF, which stimulates melanoma growth, induced nNOS expression markedly (FIG. 2F). However, nNOS inductions by UVB and DETA/NO were not evident in melanocytes (FIG. 2G).

Figure 3A:
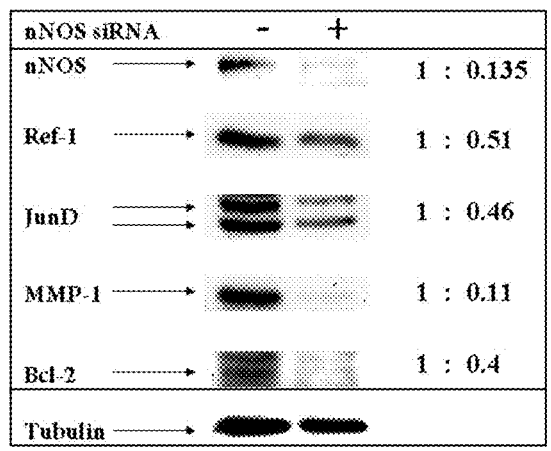
FIGS. 3A-B. (A) nNOS depletion in melanoma associated with down-regulation of genes involved in proliferation and metastasis. Metastatic melanoma cells were transfected with nNOS siRNA and whole cell lysates were collected for immunoblotting assay. (B) Reduced invasion potential in nNOS-depleted melanoma cells. The represented data was from Lu1205 cells. Same changes were also evident in A375 cells.
Figure 3B:
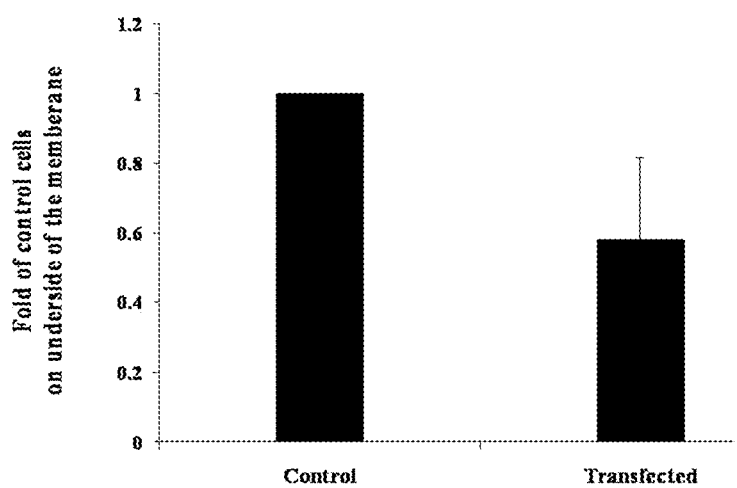

Example 3 nNOS silencing was associated with reduced invasion potential in metastatic melanoma cells. Using siRNA transfection, nNOS was transiently knocked down in two metastatic melanoma cells (A375 and Lu1205) (FIG. 3A). Immunoblotting analysis showed that with nNOS depletion, the expression levels of JunD, MMP-1, APE/Ref-1, and Bcl-2 were significantly reduced. Consistently, it was found that the invasion potential was also decreased in nNOS-depleted melanoma cells (FIG. 3B).

Example 4

Effects of nNOS inhibitor cpd 8 (JI-11) on human melanoma cells. To explore the anti-melanoma effects of nNOS inhibitors, a number of synthesized nNOS inhibitors were tested. (See, FIG. 8 and Table 1, below.) The candidate compounds with lower $K_i$/nNOS values exhibited higher binding affinity and more potent enzyme inhibition. The calculated values of $K_i$(eNOS)/$K_i$(nNOS) and $K_i$(iNOS)/$K_i$(nNOS)) represented the relative selectivity of nNOS over eNOS or iNOS, respectively. Among these compounds, cpd 8 (FIG. 4A) exhibits 3,000 fold selectivity for nNOS over eNOS and 840 fold over iNOS. Furthermore, cpd 8 binds tightly to nNOS and its $K_i$(nNOS) is very low (17.7 nM.)

Figure 4A:
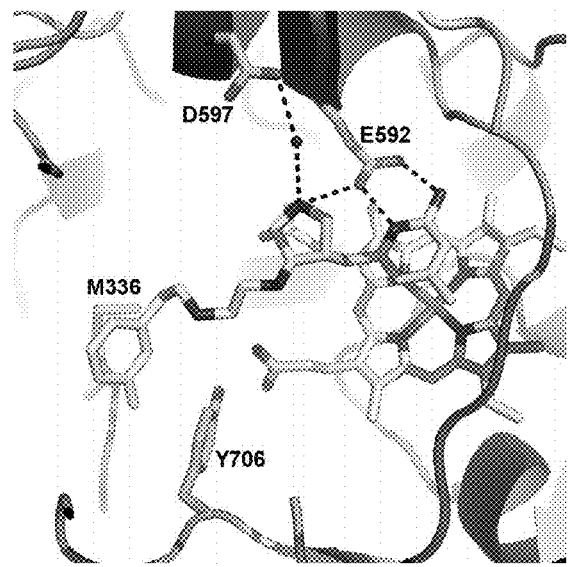
FIGS. 4A-F. Specific nNOS inhibitor cpd 8 (JI-11). (A) Docking model of cpd 8 with nNOS protein. (B) cpd 8 significantly reduced total NOS activities in human melanoma Lu1205 cells. Spermidine trihydrochloride (ST), 10 μM; cpd 8, 1 μM. Results are the means±SD of three biologic replicates of a representative experiment. *, p<0.05 compared to control cells. (C-D) cpd 8 inhibited nNOS expression induced by DETA/NO stress (C) and UVB radiation (D). (E-F) Elevated proliferation (E) and invasion potential (F) by DETA/NO stress were also reversed by cpd 8 co-treatment.
Figure 4B:
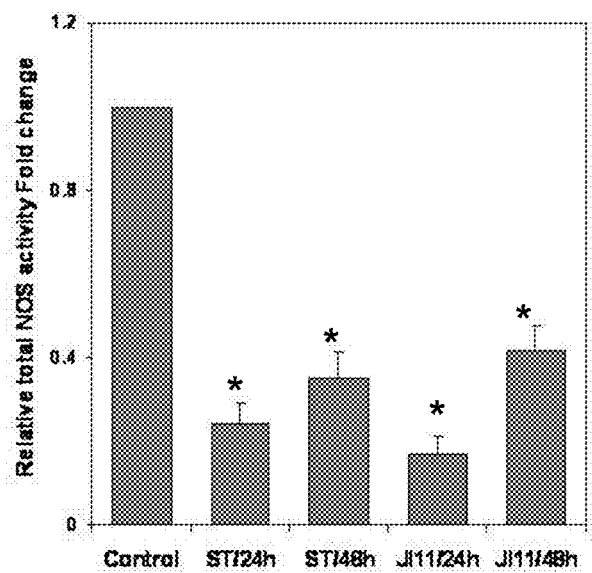

At 1 µM concentration, cpd 8 effectively inhibited the NOS activity in metastatic Lu1205 cells; however, its inhibitory activity became weakened after 48 hours, suggesting that the inhibition of nNOS by cpd 8 is potent but reversible (FIG. 4B). (By comparison, Spermidine trihydrochloride (ST), a commercially-available nNOS inhibitor, generated a comparable inhibition of NOS activity at a concentration of 10 µM.)

Figure 4C:
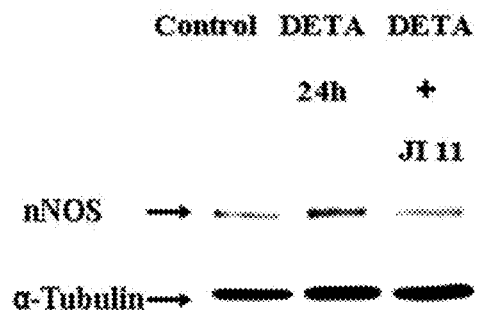
Figure 4D:
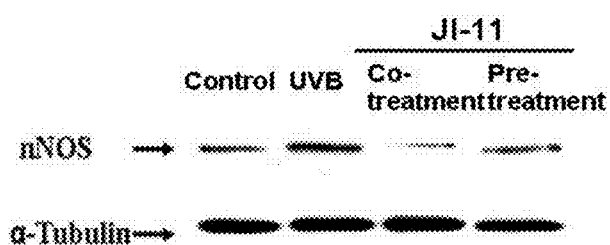
Figure 4E:
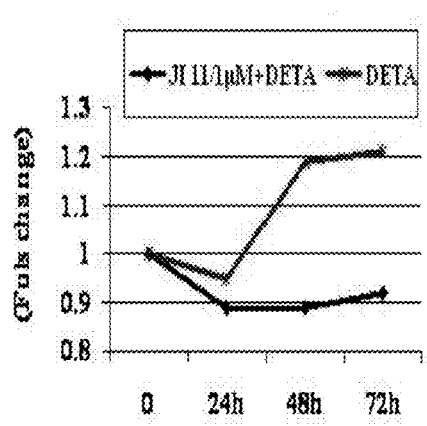
Figure 4F:
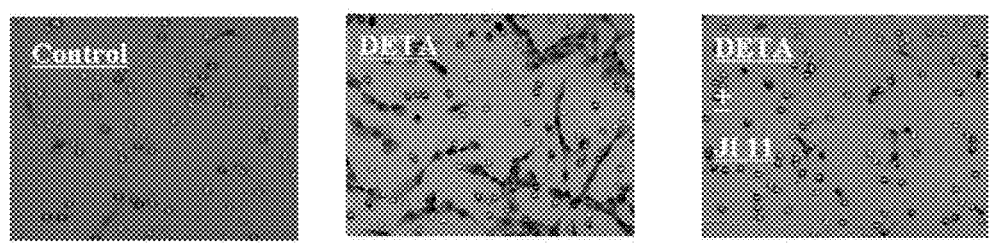

Cpd 8 does not affect basal nNOS levels of melanoma cells, even up to a concentration of 200 µM (not shown). However, at concentrations as low as 1 µM, it effectively inhibited the induction of nNOS by DETA/NO or UVB radiation treatments (FIG. 4C-D). As shown in FIG. 4E, DETA/NO-stimulated proliferation was significantly reversed by cpd 8 after 3 days. Similar reduction in cell invasion potential was also evident by cpd 8 co-treatment with DETA/NO (FIG. 4D).

TABLE 1

| Compounds | Ki (uM) | | | Selectivity | |
| --- | --- | --- | --- | --- | --- |
| | nNOS | iNOS | eNOS | nNOS/iNOS | nNOS/eNOS |
| 1 | 0.014 | 4.06 | 28 | 290 | 2000 |
| 2 | 48 | 609 | 122 | 12.7 | 2.5 |
| 3 | 0.21 | 13.6 | 116 | 64.8 | 552.4 |
| 4 | 0.88 | 18.2 | 123.9 | 20.7 | 140.8 |
| 5 | 0.098 | 5.84 | 282.9 | 59.6 | 2886.7 |
| 6 | 0.085 | 8.95 | 85.16 | 105.3 | 1001.9 |
| 7 | 0.024 | 5.4 | 78.45 | 225 | 3268.8 |
| 8 | 0.0177 | 15 | 53.4 | 847.4 | 3017 | nNOS/iNOS represents the selectivity of nNOS over iNOS, calculated by Ki(iNOS)/Ki(nNOS));
Nnos/eNOS represents the selectivity of nNOS over eNOS, calculated by Ki(eNOS)/Ki(nNOS)

Example 5

Figure 5A:
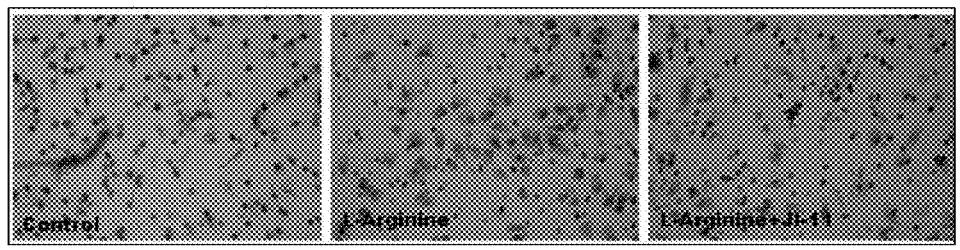
FIGS. 5A-E. L-Arginine enhanced the invasion and tumor growth of human melanoma, which is mediated by nNOS/NO generation. (A) Matrigel Invasion Analysis of melanoma A375 cells. Elevated invasion potential by L-arginine was inhibited by cpd 8 (JI-11) co-treatment. (B) Histology of melanoma growth stimulated by L-arginine in reconstructed skin equivalents, which were incubated in the absence or presence of cpd 8. The represented samples were stained with H&E. (C) The lesions occurred in 3-D skin constructs were stained positive with S-100 antibody. (D) Intracellular NO level was increased after incubation with L-arginine, which was markedly diminished by nNOS depletion in A375 cells. #, p<0.05, compared to control; *, p<0.05, compared to control siRNA/L-arginine. (E) L-Arginine-induced NO generation was only inhibited by nNOS inhibitor cpd 8 (JI-11). RES, resveratrol; CUR, curcumin. #, p<0.05, compared to control; *, p<0.05 compared to L-arginine alone.
Figure 5B:
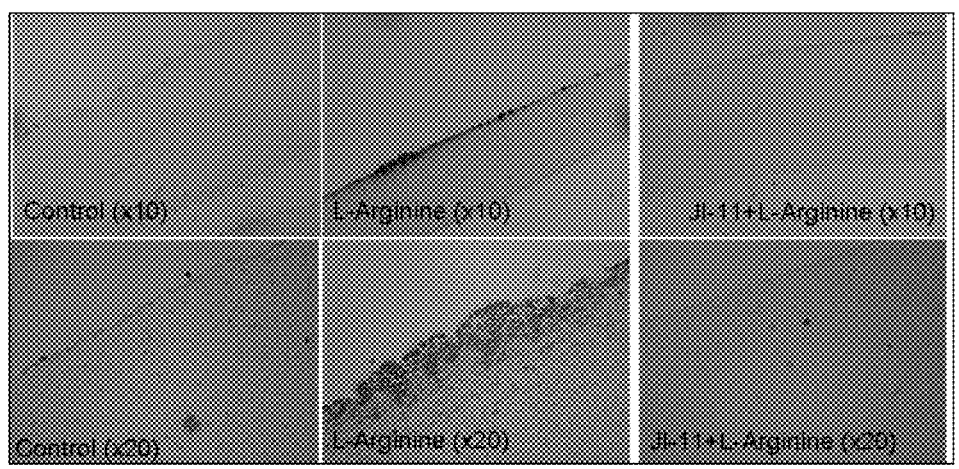
Figure 5C:

L-Arginine significantly enhanced the growth and invasion of human melanoma due to a nNOS-mediated NO stress, which is effectively inhibited by nNOS inhibitors. As shown in FIG. 5A, an in vitro matrigel-coated chamber invasion assay demonstrated that incubating metastatic melanoma cells with L-arginine (2.87 mM), a NOS substrate, markedly enhanced the invasion potential, which was efficiently reversed by co-treatment with nNOS inhibitor cpd 8 (JI-11). In addition, artificial human skin equivalents were constructed in a 3D setting, incorporating human metastatic melanoma cells, kerationcytes, and fibroblast cells on a collagen base. As shown in FIG. 5B, after 2-weeks of treatment, L-arginine significantly promoted melanoma growth compared to control and melanoma lesions spread over the epidermis layer. Some of these lesions grew deeper and invaded downward toward the dermal layer. All the lesions were stained positively for melanocyte marker S-100 (FIG. 5C). Co-treatment with nNOS inhibitor cpd 8 (2 µM) reversed the overgrowth induced by L-arginine, and the skin reconstruct samples looked much like control with a smooth epidermal surface.

Figure 5D:
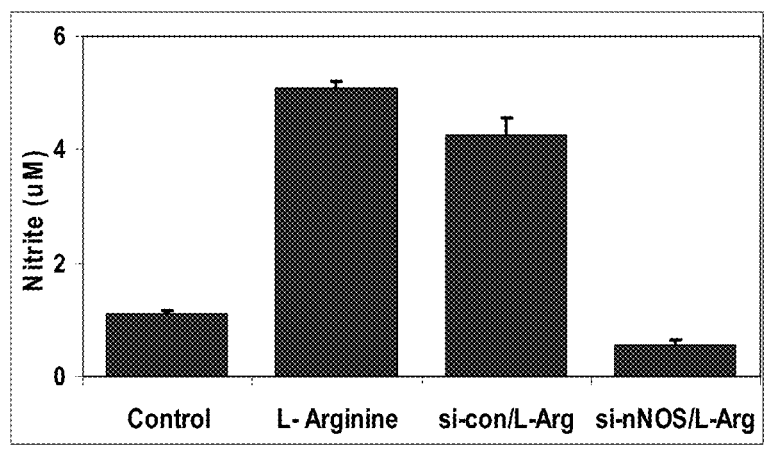
Figure 5E:
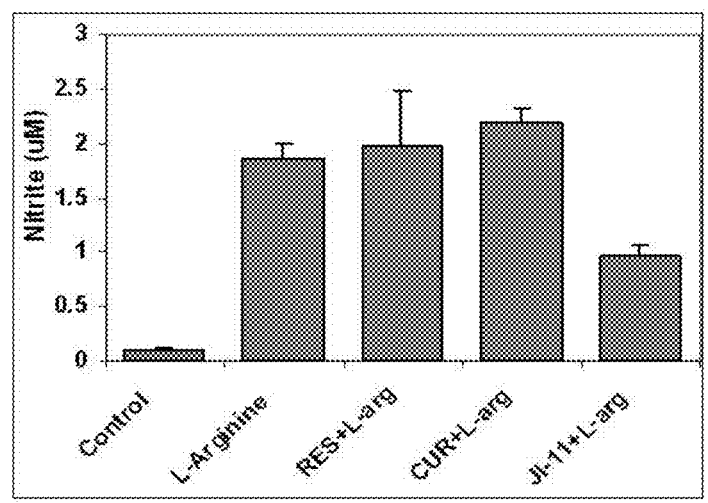

Furthermore, to investigate whether L-arginine-induced NO generation in melanoma is mediated by nNOS, nNOS-depleted cells were incubated with L-arginine and analyzed intracellular NO levels. As shown in FIG. 5D, L-arginine failed to induce NO production in nNOS-depleted melanoma cells, which indicated that L-arginine-induced NO generation was predominantly mediated by nNOS, which utilizes L-arginine as the substrate. Notably, the induction of NO levels occurred only after L-arginine exposure was reduced by nNOS inhibitor cpd 8 (FIG. 5E). Even up to 50 µM resveratrol and curcumin (two well-documented iNOS inhibitors) failed to inhibit the increase of NO by L-arginine in human melanoma cells.

Example 6

Figure 6A:
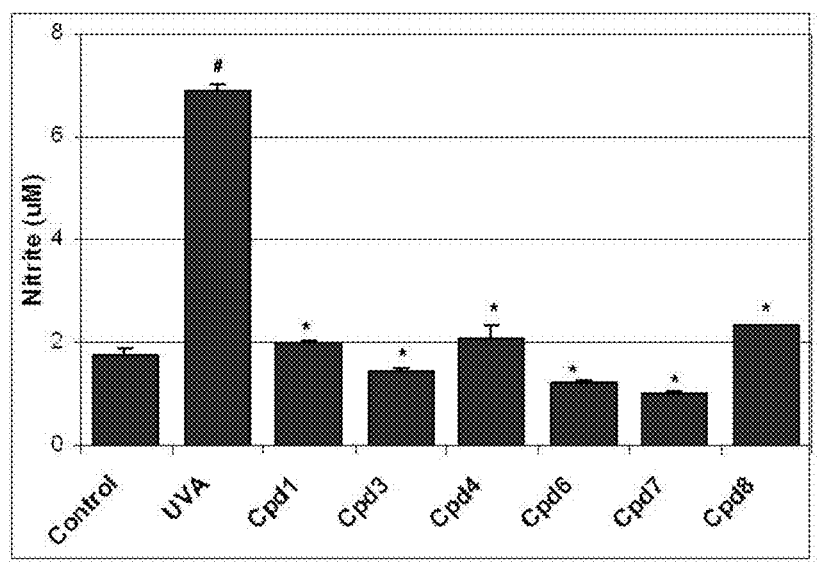
FIGS. 6A-C. Effects of novel synthesized nNOS inhibitors on human melanoma cells. (A) Inhibition of UVA radiation-induced intracellular NO generation detected by Griess reagents. #, p<0.05 compared to control; *, p<0.05 compared to UVA-treated sample; (B) Reduced invasion potential of metastatic melanoma. Bars represented the means of invaded cells counted in 20 highlight fields and normalized to control (set as 1.0). *, p<0.05 compared to control. (C) L-arginine-stimulated adhesion of metastatic melanoma A375 cells to fibroblast monolayer were inhibited by nNOS inhibitors (2 μM). The data represented in the figure is the mean changes of OD values (control is normalized as 0). *, p<0.05 compared to DMSO+L-arginine treatment.
Figure 6B:
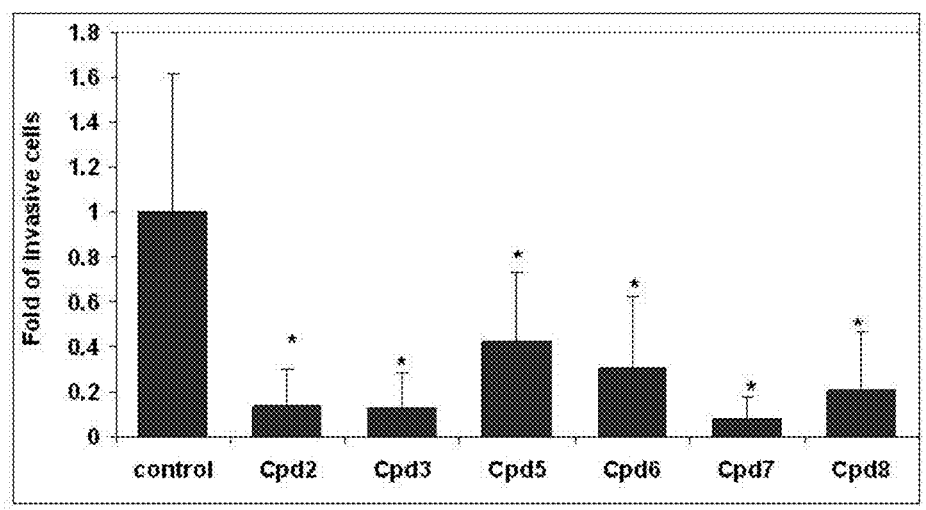
Figure 6C:
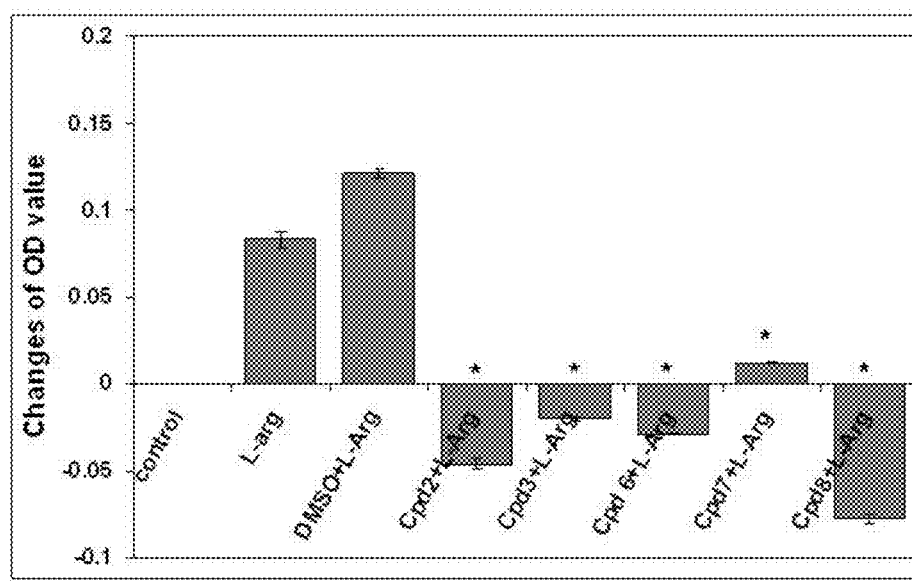

Novel nNOS inhibitors showed promising anti-melanoma activities. As shown in FIG. 6A, all tested nNOS inhibitors efficiently diminished UVA-induced NO production at 1 µM concentration. With co-treatment, NO levels in most of the samples were reduced to basal levels comparable to that of control. Treatments with these inhibitors alone also significantly reduced the invasion potential of metastatic melanoma A375 cells (FIG. 6B). Furthermore, our adhesion analysis revealed that short-term treatments with nNOS inhibitors significantly inhibited L-arginine-stimulated adhesion of metastatic A375 cells to human primary fibroblast cells (FIG. 6C). Among all the tested inhibitors at the concentration of 2 µM, cpd 8 exhibited the most potent inhibition of the relative adhesion compared to L-arginine alone.

To determine whether the inhibitions of nNOS correlated with their anti-invasive activities, linear regression analysis was employed utilizing SAS statistic software. Correlation analysis of anti-invasion potential and iNOS inhibitory potency (represented as 1/$K_i$(iNOS)) has produced an $R^2$ of 0.0153 (p=0.7917) and for nNOS inhibition potency (represented as 1/$K_i$(nNOS)), an $R^2$ value of 0.1467 (p=0.3964) was obtained.

Figure 7:
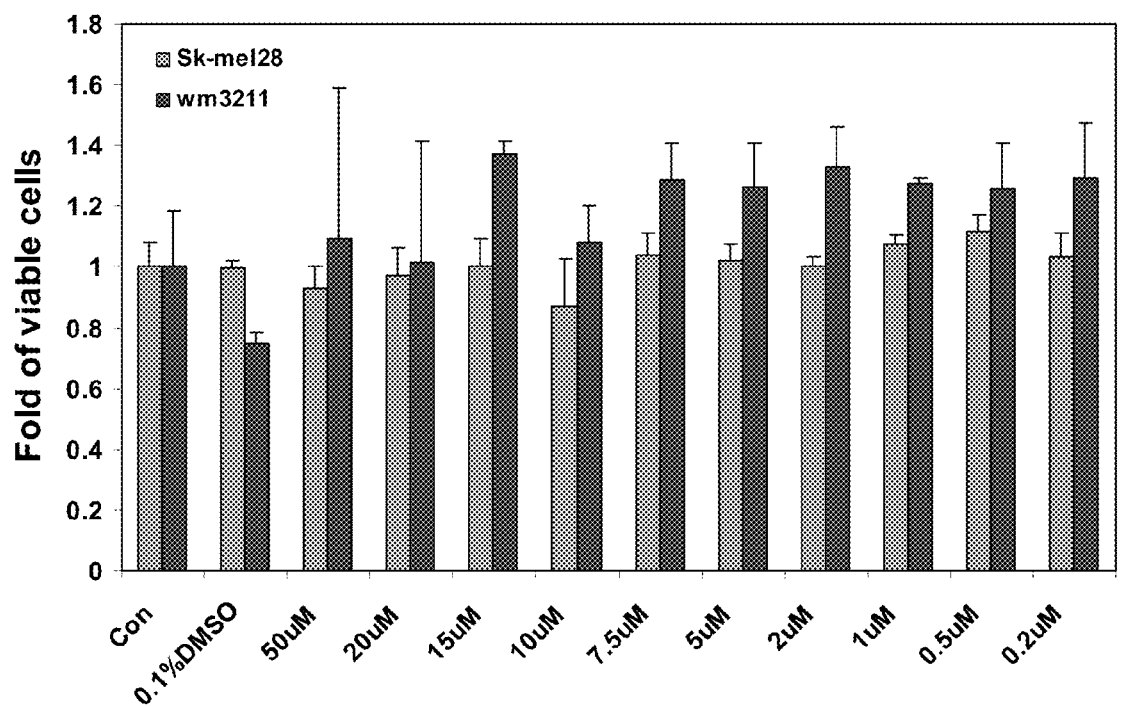
FIG. 7. Effects of cpd JI-16 (a homolog of cpd 2) on cell proliferation in human melanoma cells. MTT colorimetric assay was employed after 72-hour treatments, and the relative proliferation rate was represented as fold of control cells.

Notably, cpd 2 (Table 1) showed cytotoxicity in tested melanoma cell lines (wm3211 and Sk-Mel28), and the $IC_{50}$ was 5 µM and 3.5 µM, respectively. Toxicity may be related to the phenyl group attached to the pyrrolidine N atom since a homolog of cpd 2 (a/k/a cpd JI-16, which is the same as cpd 2 except the phenyl group is absent) does not exhibit any toxicity in melanoma cells even up to 50 µM (See, FIG. 7).

We claim:

1. A method of reducing expression of neuronal nitric oxide synthase, said method comprising:
providing a compound selected from compounds of a formula

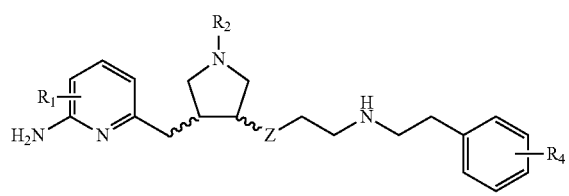

wherein $R_1$ is selected from H, halogen, methyl and halomethyl moieties; $R_2$ is selected from H, alkyl and haloalkyl moieties; Z is selected from O and NH; and $R_4$ is selected from H, alkyl, halogen and haloalkyl moieties, and salts thereof; and contacting said compound with a cellular medium comprising one of human melanocytes, melanoma cells and a combination thereof, said compound in an amount sufficient to reduce induction of neuronal nitric oxide synthase expression, thereby reducing ultra-violet induced nitric oxide production in a human melanocyte or melanoma cell.

2. The method of claim 1 wherein $R_2$ is H, Z is NH, and $R_4$ is selected from H and halogen moieties, said compound selected from cis and trans stereoisomers.

3. The method of claim 2 wherein said compound is selected from
- $N^1$-((3R,4R)-4-((6-amino-4-methylpyridin-2,yl)methyl)pyrrolidin-3-yl)-$N^2$-(3-fluorophenethyl)ethane-1,2-diamine (1);
- $N^1$-((3S,4S)-4((6-amino-4-methylplyridin-2-yl)methyl)pyrrolidin-3-yl)-$N^2$-(4-chlorobenzyl)ethane-1,2-diamine (6);
- $N^1$-((3S,4S)-4-S((6-amino-4-methylpyridin-2-yl)methyl)pyrrolidin-3-yl)-$N^2$-phenethylethane-1,2-diamine (7); and
- $N^1$-((3R,4S)-4-((6-amino-4-methylpyridin-2-l)methyl)pyrrolidin-3-yl)-$N^2$-(3- fluorophenethyl)ethane-1,2-diamine (8), 4. The method of claim 1 wherein said compound is an ammonium salt.

5. The method of claim 4 wherein said ammonium salt has a counter ion that is a conjugate base of a protic acid.

6. The method of claim 1 wherein said compound is provided in a pharmaceutical composition.

7. The method of claim 1 wherein $R_1$ is selected from H and methyl.

8. The method of claim 7 wherein $R_2$ is H and Z is NH.

9. The method of claim 8 wherein $R_4$ is selected from H and halogen moieties.

10. The method of claim 9 wherein said compound is selected from cis and trans stereoisomers.

11. The method of claim 10 wherein said compound is provided in a pharmaceutical composition.

12. The method of claim 7 wherein said compound is selected from
- $N^1$-((3R,4R)-4-((6-amino-4-methylpyridin-2-yl)pyrrolidin-3-yl)-$N^2$-(3-fluorophenethyl)pethane-1,2-diamine (1);
- N-$^1$((3S,4S)-4((6-amino-4-methylpyridin-2-yl)methyl)pyrrolidin-3-yl)-$N^2$-(4-chlorobenzyl)ethane-1,2-diamine (6);
- $N^1$-((3S,4S)-4-((6-amino-4-methylpyridin-2-yl)methyp-pyrrolidin-3-yl)-$N^2$-phenethylethane-1,2-diamine (7); and
- $N^1$-((3R,4S)-4-((6-amino-4-methylpyridin-2-yl)methyl)pyrrolidin-3-yl)-$N^2$(3- fluorophenethyl)ethane-1,2-diamine (8).

13. The method of claim 12 wherein said compound is an ammonium salt.

14. The method of claim 13 wherein said ammonium salt has a counter ion that is a conjugate base of a protic acid.

15. The method of claim 14 wherein said compound is provided in a pharmaceutical composition.

* * * * *